United States Patent
Bartlett et al.

(10) Patent No.: US 7,353,215 B2
(45) Date of Patent: Apr. 1, 2008

(54) KERNELS AND METHODS FOR SELECTING KERNELS FOR USE IN LEARNING MACHINES

(75) Inventors: Peter L. Bartlett, Berkeley, CA (US); André Elisseeff, Thalwil (CH); Bernhard Schoelkopf, Tübingen (DE)

(73) Assignee: Health Discovery Corporation, Savannah, GA (US)

( * ) Notice: Subject to any disclaimer, the term of this patent is extended or adjusted under 35 U.S.C. 154(b) by 265 days.

(21) Appl. No.: 10/477,078

(22) PCT Filed: May 7, 2002

(86) PCT No.: PCT/US02/14311

§ 371 (c)(1),
(2), (4) Date: Nov. 7, 2003

(87) PCT Pub. No.: WO02/091211

PCT Pub. Date: Nov. 14, 2002

(65) Prior Publication Data

US 2005/0071300 A1   Mar. 31, 2005

(51) Int. Cl.
G06F 17/00 (2006.01)
G06N 5/02 (2006.01)

(52) U.S. Cl. .............................. 706/46; 706/45; 706/12

(58) Field of Classification Search .................. 706/12, 706/46, 45; 707/101
See application file for complete search history.

(56) References Cited

U.S. PATENT DOCUMENTS 5,649,068 A  7/1997  Boser et al.
5,950,146 A  9/1999  Vapnik
6,128,608 A  10/2000  Barnhill
6,157,921 A  12/2000  Barnhill
6,267,722 B1  7/2001  Anderson et al.
6,427,141 B1  7/2002  Barnhill
6,658,395 B1  12/2003  Barnhill
6,714,925 B1  3/2004  Barnhill et al.
6,760,715 B1  7/2004  Barnhill et al.
6,789,069 B1  9/2004  Barnhill et al.

(Continued)

OTHER PUBLICATIONS

Patrice Y. Simard et al., Transformation Invariance in Pattern a Rcognition-Tangent Distance and Tangent Propagation, 1998, Image Processing Services Research Lab, pp. 1-33.*

(Continued)

*Primary Examiner*—Joseph P Hirl
(74) *Attorney, Agent, or Firm*—Procopio, Cory, Hargreaves & Savitch LLP; Eleanor M. Musick

(57) ABSTRACT

Learning machines, such as support vector machines, are used to analyze datasets to recognize patterns within the dataset using kernels that are selected according to the nature of the data to be analyzed. Where the datasets possesses structural characteristics, locational kernels can be utilized to provide measures of similarity among data points within the dataset. The locational kernels are then combined to generate a decision function, or kernel, that can be used to analyze the dataset. Where invariance transformations or noise is present, tangent vectors are defined to identify relationships between the invariance or noise and the data points. A covariance matrix is formed using the tangent vectors, then used in generation of the kernel for recognizing patterns in the dataset.

23 Claims, 11 Drawing Sheets

U.S. PATENT DOCUMENTS

| | | |
|---|---|---|
| 6,882,990 B1 | 4/2005 | Barnhill et al. |
| 6,944,602 B2 | 9/2005 | Cristianini |
| 2003/0172043 A1 | 9/2003 | Guyon et al. |

OTHER PUBLICATIONS

Amir Ben-Dor et al., Tissue Classification with Gene Expression Profiles, 2000, RECOMB, pp. 54-64.*

Mario A.T. Figueiredo, On Gaussian Radial basis Function Approximations: Interpretation, Extensions, and Learning Strategies, Sep. 2000, IEEE, pp. 618-621.*

Barash, et al., "Context-Specific Bayesian Clustering for Gene Expression Data", *Proceedings of the 5th Annual International Conference on Computational Biology*, Apr. 2001, pp. 12-21.

Ben-Dor et al., "Tissue Classification with Gene Expression Profiles", *Proceedings of the 4th Annual International Conference on Computational Molecular Biology*, Apr. 2000, pp. 54-64.

Burges, C. J. C., "Geometry and Invariance in Kernel Based Methods", *Advances in Kernel Methods—Support Vector Learning*, Edited by Schölkopf, Burges, and Smola, 1999, MIT Press.

Chapelle, O., et al., "Choosing Multiple Parameters for Support Vector Machines", *Machine Learning*, 2002, pp. 131-159, vol. 46, No. 1.

Decoste, D., et al., M. C., "Distortion-Invariant Recognition Via Jittered Queries.", *Computer Vision and Pattern Recognition (CVPR-2000)*, Jun. 2000.

Decoste, D., et al., "Training Invariant Support Vector Machines", *Machine Learning*, 2002, vol. 46, No. 3.

Haussler, D., "Convolutional Kernels on Discrete Structures", *Technical Report UCSC-CRL-99-10, Computer Science Department, University of California at Santa Cruz*, 1999.

Hoffman et al., "DNA Visual and Analytical Data Mining", *Proceedings of the 8th Conference on Visualization*, Oct. 1997, pp. 437-441, (Abstract).

Lathrop et al., "Massively Parallel Symbolic Induction of Protein Structure/Function Relationship", *Proceedings of the 27th Hawaii International Conference on System Sciences*, Jan. 1991, vol. 1, pp. 585-594, (Abstract).

Leen, T., "From Data Distributions to Regularization in Invariant Learning", *Advances in Neural Information Processing Systems*, 1995, vol. 7.

Lodhi, H., et al., "Text Classification Using String Kernels", Technical Report 2000-79, NeuroCOLT, 2000, *Advances in Neural Information Processing Systems*, Edited by T. K. Leen, T. G. Dietterich, and V. Tresp, 2001, vol. 13, MIT Press.

McCallum et al., "Efficient Clustering of High-Dimensional Data Sets with Application to Reference Matching", *Proceedings of the 6th ACM SIGKDD International Conference on Knowledge Discovery and Data Mining*, Aug. 2000, pp. 169-178.

Niyogi, P., "Incorporation Prior Information in Machine Learning by Creating Virtual Examples", *IEEE Proceedings on Intelligent Signal Processing*, Nov. 1998, pp. 2196-2209, 86(11).

Pavlidis et al., "Gene Functional Classification From heterogeneous Data", *Proceedings of the 5th Annual International Conference on Computational Biology*, Apr. 2001, pp. 249-255.

Platt, J., "Probabilities for Support Vector Machines", *Advances in Large Margin Classifiers*, Edited by Smola, Bartlett, Schölkopf, and Scbuurmans, 2000, MIT Press, Cambridge, MA.

Schölkopf, B., et al., "Extracting Support Data for a Given Task", *First International Conference on knowledge Discovery & Data Mining*, 1995, AAAI Press, (Abstract).

Schölkopf, B., et al., "Generalization Bounds Via, Elgenvalues of the Gram Matrix", *Technical report 99-035, NeuroColt*, 1999.

Schölkopf, B., et al., "Nonlinear Component Analysis as a Kernel Eigenvalue Problems", *Neural Computation*, 1998, pp. 1299-1319, vol. 10.

Schölkopf, B., et al., "Prior Knowledge in Support Vector Kernels", *Advances in Neural Information Processing Systems*, 1998, pp. 640-646, vol. 10, MIT Press, Cambridge, MA.

Simard, P., et al., "Transformation Invariance in Pattern Recognition—Tangent Distance and Tangent Propagation", *Neural networks: Tricks of the Trade*, 1998, Springer.

Smola, A. J., et al., "Sparse Greedy Matrix Approximation for Machine Learning", *Proceedings of the 17th International Conference on Machine Learning*, 2000, pp. 911-918, Morgan Kaufman, San Francisco.

Tsuda. K., "Support Vector Classifier with Asymmetric Kernel Function", *Proceedings of ESANN'99*, 1999, pp. 183-188.

Williams, C., et al., "Using the Nystrom Method to Speed Up Kernel Machines", *Advances in Neural Information Processing Systems*, 2001, pp. 682-688, vol. 13, MIT Press.

Zien, A., et al., "Engineering Support Vector Machine Kernels That Recognize translation Initiation Sites", *Bioinformatics*, 2000, 799-807, 16(9).

* cited by examiner

KERNELS AND METHODS FOR SELECTING KERNELS FOR USE IN LEARNING MACHINES

FIELD OF THE INVENTION

The present invention relates to the use of learning machines to identify relevant patterns in datasets containing large quantities of diverse data, and more particularly to a method and system for selection of kernels to be used in kernel machines which best enable identification of relevant patterns.

BACKGROUND OF THE INVENTION

In recent years, machine-learning approaches for data analysis have been widely explored for recognizing patterns which, in turn, allow extraction of significant information contained within a large data set that may also include data consisting of nothing more than irrelevant detail. Learning machines comprise algorithms that may be trained to generalize using data with known outcomes. Trained learning machine algorithms may then be applied to predict the outcome in cases of unknown outcome, i.e., to classify the data according to learned patterns. Machine-learning approaches, which include neural networks, hidden Markov models, belief networks and kernel-based classifiers such as support vector machines, are ideally suited for domains characterized by the existence of large amounts of data, noisy patterns and the absence of general theories. Support vector machines are disclosed in U.S. Pat. Nos. 6,128,608 and 6,157,921, both of which are assigned to the assignee of the present application and are incorporated herein by reference.

Many successful approaches to pattern classification, regression, clustering, and novelty detection problems rely on kernels for determining the similarity of a pair of patterns. These kernels are usually defined for patterns that can be represented as a vector of real numbers. For example, the liner kernels, radial basis function kernels, and polynomial kernels all measure the similarity of a pair of real vectors. Such kernels are appropriate when the patterns are best represented in this way, as a sequence of real numbers. The choice of a kernel corresponds to the choice of representation of the data in a feature space. In many applications, the patterns have a greater degree of structure. This structure can be exploited to improve the performance of the learning system. Examples of the types of structured data that commonly occur in machine learning applications are strings, such as DNA sequences, and documents; trees, such as parse trees used in natural language processing; graphs, such as web sites or chemical molecules; signals, such as ECG signals and microarray expression profiles; spectra; images; spatio-temporal data; and relational data, among others.

For structural objects, kernels methods are often applied by first finding a mapping from the structured objects to a vector of real numbers. In one embodiment of the kernel selection method, the invention described herein provides an alternative approach which may be applied to the selection of kernels which may be used for structured objects.

Many problems in bioinformatics, chemistry and other industrial processes involve the measurement of some features of samples by means of an apparatus whose operation is subject to fluctuations, influenced for instance by the details of the preparation of the measurement, or by environmental conditions such as temperature. For example, analytical instruments that rely on scintillation crystals for detecting radiation are known to be temperature sensitive, with additional noise or signal drift occurring if the crystals are not maintained within a specified temperature range. Data recorded using such measurement devices is subject to problems in subsequent processing, which can include machine learning methods. Therefore, it is desirable to provide automated ways of dealing with such data.

In certain classification tasks, there is a priori knowledge about the invariances related to the task. For instance, in image classification, it is known that the label of a given image should not change after a small translation or rotation. In a second embodiment of the method for selecting kernels for kernel machines, to improve performance, prior knowledge such as known transformation invariances or noise distribution is incorporated in the kernels. A technique is disclosed in which noise is represented as vectors in a feature space. The noise vectors are taken into account in constructing invariant kernel classifiers to obtain a decision function that is invariant with respect to the noise.

BRIEF SUMMARY OF THE INVENTION

According to the present invention, methods are provided for selection and construction of kernels for use in kernel machines such that the kernels are suited to analysis of data which may posses characteristics such as structure, for example DNA sequences, documents; graphs, signals, such as ECG signals and microarray expression profiles; spectra; images; spatio-temporal data; and relational data, and which may possess invariances or noise components that can interfere with the ability to accurately extract the desired information.

In an exemplary embodiment, in a method for defining a similarity measure for structured objects, a location-dependent kernel is defined on one or more structures that comprise patterns in the structured data of a data set. This locational kernel defines a notion of similarity between structures that is relevant to particular locations in the structures. Using the locational kernel, a pair of structures can be viewed according to the similarities of their components. Multiple locational kernels can then be used to obtain yet another locational kernel. A kernel on the set of structures can be then obtained by combining the locational kernel(s). Different methods for combining the locational kernels include summing the locational kernels over the indices, fixing the indices, and taking the product over all index positions of locational kernels constructed from Gaussian radial basis function (RBF) kernels whose indices have been fixed. The resulting kernels are then used for processing the input data set.

The method of the present invention comprises the steps of: representing a structured object as a collection of component objects, together with their location within the structure; defining kernels, called locational kernels, that measure the similarity of (structure, location in structure) pairs; constructing locational kernels from kernels defined on the set of components; constructing locational kernels from other locational kernels; and constructing kernels on structured objects by combining locational kernels.

An iterative process comparing postprocessed training outputs or test outputs can be applied to make a determination as to which kernel configuration provides the optimal solution. If the test output is not the optimal solution, the selection of the kernel may be adjusted and the support vector machine may be retrained and retested. Once it is determined that the optimal solution has been identified, a live data set may be collected and preprocessed in the same manner as was the training data set to select the features that best represent the data. The pre-processed live data set is input into the learning machine for processing.

In an exemplary application of the kernel selection techniques of the first embodiment, a locational kernel construction scheme is used for comparing infrared spectra to classify disease states.

In a second embodiment, another component of kernel selection and design involves incorporating noise information into the kernel so that invariances are introduced into the learning system. The noise of the instrument that was used to generate the data can provide information that can be used in kernel design. For example, if certain peaks in a spectrum always have the same value while other peaks have values that vary with different experimental settings, the system takes this into account in its calculations. One method of compensation comprises normalizing every peak value. Analysis of control classes to infer the variability across different instruments can be incorporated into the kernel.

While the inventive methods disclosed herein are contemplated for use in different types of kernel machines, in an exemplary implementation, the kernel machine is a support vector machine. The exemplary system comprises a storage device for storing a training data set and a test data set, and a processor for executing a support vector machine. The processor is also operable for collecting the training data set from the database, pre-processing the training data set, training the support vector machine using the pre-processed training data set, collecting the test data set from the database, pre-processing the test data set in the same manner as was the training data set, testing the trained support vector machine using the pre-processed test data set, and in response to receiving the test output of the trained support vector machine, post-processing the test output to determine if the test output is an optimal solution. The exemplary system may also comprise a communications device for receiving the test data set and the training data set from a remote source. In such a case, the processor may be operable to store the training data set in the storage device prior pre-processing of the training data set and to store the test data set in the storage device prior pre-processing of the test data set. The exemplary system may also comprise a display device for displaying the post-processed test data. The processor of the exemplary system may further be operable for performing each additional function described above.

In an exemplary embodiment, a system and method are provided for enhancing knowledge discovery from data using multiple learning machines in general and multiple support vector machines in particular. Training data for a learning machine is pre-processed. Multiple support vector machines, each comprising distinct kernels, are trained with the preprocessed training data and are tested with test data that is pre-processed in the same manner. The test outputs from multiple support vector machines are compared in order to determine which of the test outputs if any represents an optimal solution. Selection of one or more kernels may be adjusted and one or more support vector machines may be retrained and retested. When it is determined that an optimal solution has been achieved, live data is pre-processed and input into the support vector machine comprising the kernel that produced the optimal solution. The live output from the learning machine may then be post-processed as needed to place the output in a format appropriate for interpretation by a human or another computer.

BRIEF DESCRIPTION OF THE DRAWINGS

FIG. 8a represents test error for different learning algorithms against the width of a RBF kernel and $\gamma$ fixed to 0.9.

DETAILED DESCRIPTION OF THE PREFERRED EMBODIMENTS

Figure 1:
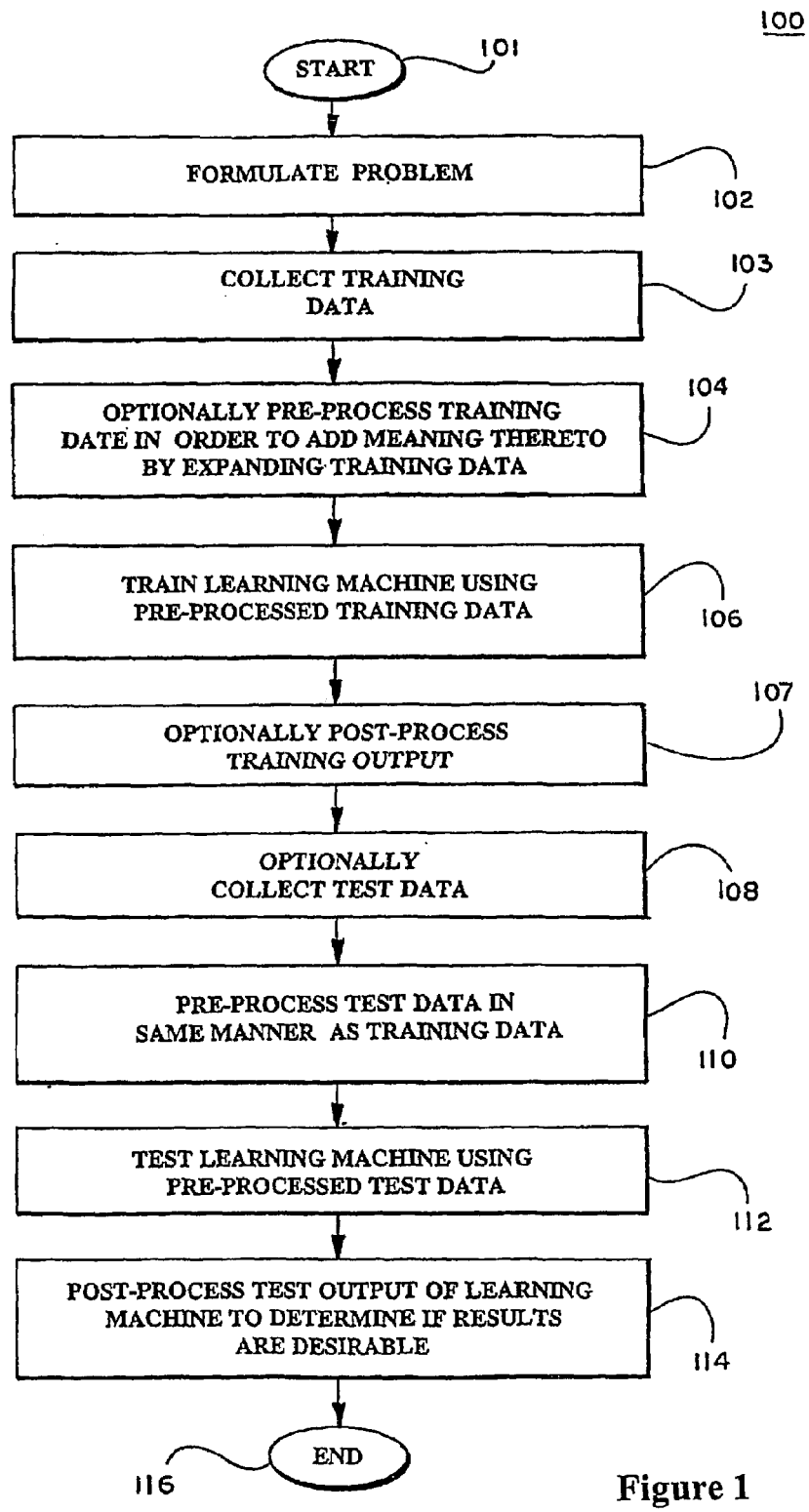
FIG. 1 is a flowchart illustrating an exemplary general method for increasing knowledge that may be discovered from data using a learning machine.

The present invention provides methods, systems and devices for discovering knowledge from data using learning machines. Particularly, the present invention is directed to methods, systems and devices for knowledge discovery from data using learning machines that are provided information regarding changes in biological systems. More particularly, the present invention comprises methods of use of such knowledge for diagnosing and prognosing changes in biological systems such as diseases. Additionally, the present invention comprises methods, compositions and devices for applying such knowledge to the testing and treating of individuals with changes in their individual biological systems. Preferred embodiments comprise detection of genes involved with prostate cancer and use of such information for treatment of patients with prostate cancer.

As used herein, "biological data" means any data derived from measuring biological conditions of human, animals or other biological organisms including microorganisms, viruses, plants and other living organisms. The measurements may be made by any tests, assays or observations that are known to physicians, scientists, diagnosticians, or the like. Biological data may include, but is not limited to, clinical tests and observations, physical and chemical measurements, genomic determinations, proteomic determinations, drug levels, hormonal and immunological tests, neurochemical or neurophysical measurements, mineral and vitamin level determinations, genetic and familial histories, and other determinations that may give insight into the state of the individual or individuals that are undergoing testing. Herein, the use of the term "data" is used interchangeably with "biological data".

While several examples of learning machines exist and advancements are expected in this field, the exemplary embodiments of the present invention focus on kernel-based learning machines and more particularly on the support vector machine.

The present invention can be used to analyze biological data generated at multiple stages of investigation into biological functions, and further, to integrate the different kinds of data for novel diagnostic and prognostic determinations. For example, biological data obtained from clinical case information, such as diagnostic test data, family or genetic histories, prior or current medical treatments, and the clinical outcomes of such activities, can be utilized in the methods, systems and devices of the present invention. Additionally, clinical samples such as diseased tissues or fluids, and normal tissues and fluids, and cell separations can provide biological data that can be utilized by the current invention. Proteomic determinations such as 2-D gel, mass spectrophotometry and antibody screening can be used to establish databases that can be utilized by the present invention. Genomic databases can also be used alone or in combination with the above-described data and databases by the present invention to provide comprehensive diagnosis, prognosis or predictive capabilities to the user of the present invention.

A first aspect of the present invention facilitates analysis of data by pre-processing the data prior to using the data to train a learning machine and/or optionally post-processing the output from a learning machine. Generally stated, pre-processing data comprises reformatting or augmenting the data in order to allow the learning machine to be applied most advantageously. In some cases, pre-processing involves selecting a method for reducing the dimensionality of the feature space, i.e., selecting the features which best represent the data. Methods which may be used for this purpose include recursive feature elimination (RFE) and elimination of data points based on expert knowledge, e.g., knowledge that measurement at ends of the measurement range tend to be predominantly noise. The features remaining after feature selection are then used to train a learning machine for purposes of pattern classification, regression, clustering and/or novelty detection.

The learning machine is a kernel machine in which the kernels are selected in consideration of certain characteristics of the data. In one embodiment, the data has a structure which permits locational kernels to be defined. These locational kernels are then used to identifying similarities between components of structures in the dataset. The locational kernels are then combined through one or more of a variety of possible operations to derive the kernel function. In another embodiment, the input dataset includes invariance or noise. The invariance or noise is taken into consideration when selecting the kernel function. Virtual support vectors may be added, or a set of tangent vectors may be generated. In preferred embodiment the kernel machine is a support vector machine.

In a manner similar to pre-processing, post-processing involves interpreting the output of a learning machine in order to discover meaningful characteristics thereof. The meaningful characteristics to be ascertained from the output may be problem- or data-specific. Post-processing involves interpreting the output into a form that, for example, may be understood by or is otherwise useful to a human observer, or converting the output into a form which may be readily received by another device for, e.g., archival or transmission.

FIG. 1 is a flowchart illustrating a general method 100 for analyzing data using learning machines. The method 100 begins at starting block 101 and progresses to step 102 where a specific problem is formalized for application of analysis through machine learning. Particularly important is a proper formulation of the desired output of the learning machine. For instance, in predicting future performance of an individual equity instrument, or a market index, a learning machine is likely to achieve better performance when predicting the expected future change rather than predicting the future price level. The future price expectation can later be derived in a post-processing step as will be discussed later in this specification.

After problem formalization, step 103 addresses training data collection. Training data comprises a set of data points having known characteristics. This data may come from customers, research facilities, academic institutions, national laboratories, commercial entities or other public or confidential sources. The source of the data and the types of data provided are not crucial to the methods. Training data may be collected from one or more local and/or remote sources. The data may be provided through any means such as via the internet, server linkages or discs, CD/ROMs, DVDs or other storage means. The collection of training data may be accomplished manually or by way of an automated process, such as known electronic data transfer methods. Accordingly, an exemplary embodiment of the learning machine for use in conjunction with the present invention may be implemented in a networked computer environment. Exemplary operating environments for implementing various embodiments of the learning machine will be described in detail with respect to FIGS. 4-5.

At step 104, the collected training data is optionally pre-processed in order to allow the learning machine to be applied most advantageously toward extraction of the knowledge inherent to the training data. During this preprocessing stage a variety of different transformations can be performed on the data to enhance its usefulness. Such transformations, examples of which include addition of expert information, labeling, binary conversion, Fourier transformations, etc., will be readily apparent to those of skill in the art. However, the preprocessing of interest in the present invention is the reduction of dimensionality by way of feature selection, different methods of which are described in detail below.

Returning to FIG. 1, an exemplary method 100 continues at step 106, where the learning machine is trained using the pre-processed data. As is known in the art, a learning machine is trained by adjusting its operating parameters until a desirable training output is achieved. The determination of whether a training output is desirable may be accomplished either manually or automatically by comparing the training output to the known characteristics of the training data. A learning machine is considered to be trained when its training output is within a predetermined error threshold from the known characteristics of the training data. In certain situations, it may be desirable, if not necessary, to post-process the training output of the learning machine at step 107. As mentioned, post-processing the output of a learning machine involves interpreting the output into a meaningful form. In the context of a regression problem, for example, it may be necessary to determine range categorizations for the output of a learning machine in order to determine if the input data points were correctly categorized. In the example of a pattern recognition problem, it is often not necessary to post-process the training output of a learning machine.

At step 108, test data is optionally collected in preparation for testing the trained learning machine. Test data may be collected from one or more local and/or remote sources. In practice, test data and training data may be collected from the same source(s) at the same time. Thus, test data and training data sets can be divided out of a common data set and stored in a local storage medium for use as different input data sets for a learning machine. Regardless of how the test data is collected, any test data used must be pre-processed at step 110 in the same manner as was the training data. As should be apparent to those skilled in the art, a proper test of the learning may only be accomplished by using testing data of the same format as the training data. Then, at step 112 the learning machine is tested using the pre-processed test data, if any. The test output of the learning machine is optionally post-processed at step 114 in order to determine if the results are desirable. Again, the post processing step involves interpreting the test output into a meaningful form. The meaningful form may be one that is readily understood by a human or one that is compatible with another processor. Regardless, the test output must be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations. The method 100 ends at step 116.

Figure 2:
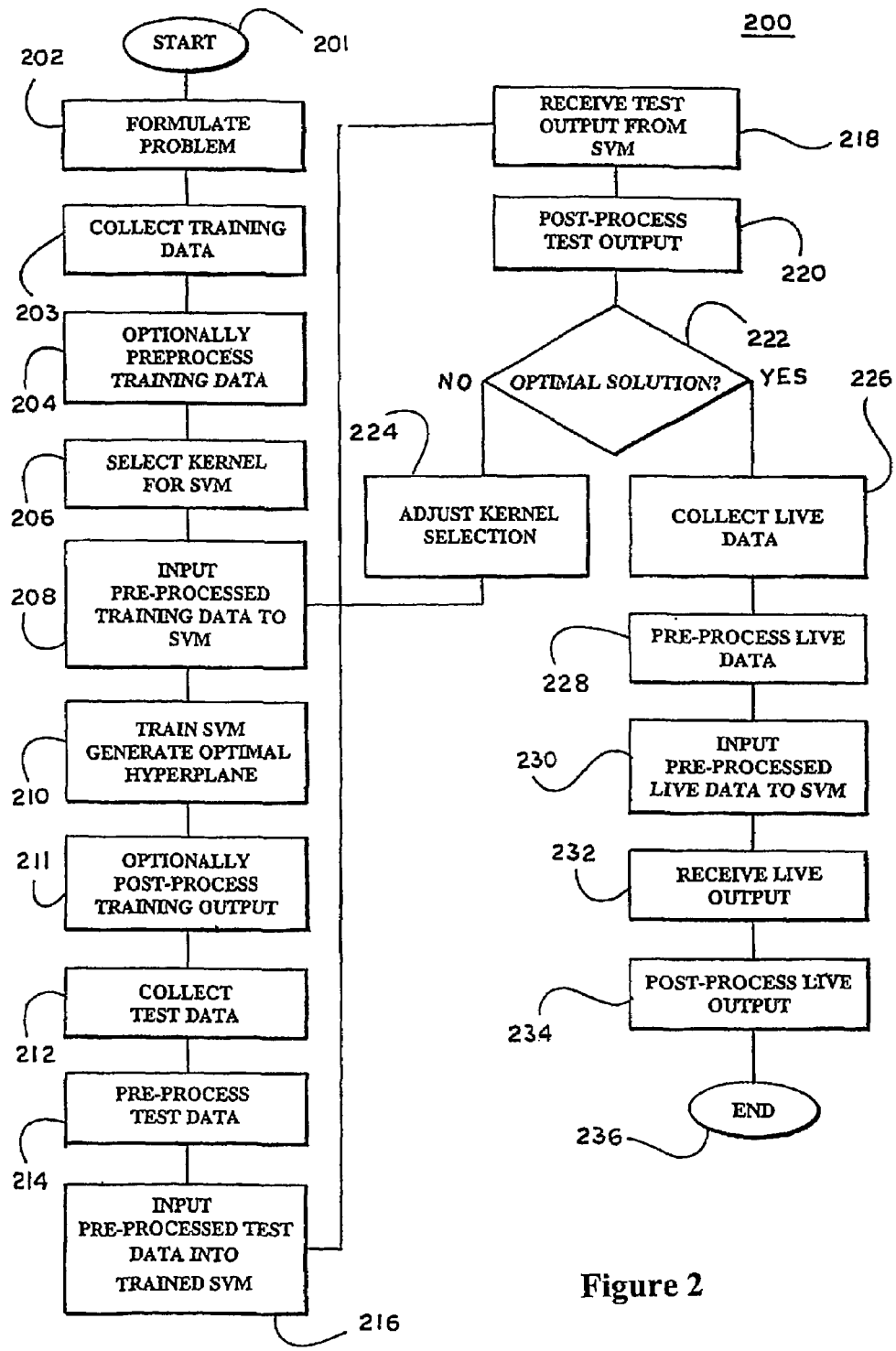
FIG. 2 is a flowchart illustrating an exemplary method for increasing knowledge that may be discovered from data using a support vector machine.

FIG. 2 is a flow chart illustrating an exemplary method 200 for enhancing knowledge that may be discovered from data using a specific type of learning machine known as a support vector machine (SVM). A SVM implements a specialized algorithm for providing generalization when estimating a multi-dimensional function from a limited collection of data. A SVM may be particularly useful in solving dependency estimation problems. More specifically, a SVM may be used accurately in estimating indicator functions (e.g. pattern recognition problems) and real-valued functions (e.g. function approximation problems, regression estimation problems, density estimation problems, and solving inverse problems). The SVM was originally developed by Boser, Guyon and Vapnik ("A training algorithm for optimal margin classifiers", *Fifth Annual Workshop on Computational Learning Theory*, Pittsburgh, ACM (1992) pp. 142-152). The concepts underlying the SVM are also explained in detail in Vapnik's book, entitled *Statistical Learning Theory* (John Wiley & Sons, Inc. 1998), which is herein incorporated by reference in its entirety. Accordingly, a familiarity with SVMs and the terminology used therewith are presumed throughout this specification.

The exemplary method 200 begins at starting block 201 and advances to step 202, where a problem is formulated and then to step 203, where a training data set is collected. As was described with reference to FIG. 1, training data may be collected from one or more local and/or remote sources, through a manual or automated process. At step 204 the training data is optionally pre-processed. Those skilled in the art should appreciate that SVMs are capable of processing input data having extremely large dimensionality, however, according to the present invention, pre-processing includes the use of feature selection methods to reduce the dimensionality of feature space.

At step 206 a kernel is selected for the SVM. As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge. As is known in the art, exemplary kernels include polynomial kernels, radial basis classifier kernels, linear kernels, etc. In an alternate embodiment, a customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel. In one of the preferred embodiments of the invention which is particularly advantageous for use with structured data, locational kernels are defined to exploit patterns within the structure. The locational kernels are then used to construct kernels on the structured object. Further discussion of the kernels for structured data is provided below. Still another embodiment incorporates noise data into selection and construction of kernels in order to facilitate extraction of relevant knowledge from noise such as measurement artifacts and other variables that may impair the accuracy of the analysis. This method for construction kernels is also described below in more detail.

At step 208 the pre-processed training data is input into the SVM. At step 210, the SVM is trained using the pre-processed training data to generate an optimal hyperplane. Optionally, the training output of the SVM may then be post-processed at step 211. Again, post-processing of training output may be desirable, or even necessary, at this point in order to properly calculate ranges or categories for the output. At step 212 test data is collected similarly to previous descriptions of data collection. The test data is pre-processed at step 214 in the same manner as was the training data above. Then, at step 216 the pre-processed test data is input into the SVM for processing in order to determine whether the SVM was trained in a desirable manner. The test output is received from the SVM at step 218 and is optionally post-processed at step 220.

Based on the post-processed test output, it is determined at step 222 whether an optimal minimum was achieved by the SVM. Those skilled in the art should appreciate that a SVM is operable to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM. Accordingly, at step 222, determining whether the optimal minimum has been ascertained may involve comparing the output of a SVM with a historical or predetermined value. Such a predetermined value may be dependant on the test data set. For example, in the context of a pattern recognition problem where data points are classified by a SVM as either having a certain characteristic or not having the characteristic, a global minimum error of 50% would not be optimal. In this example, a global minimum of 50% is no better than the result that would be achieved by flipping a coin to determine whether the data point had that characteristic. As another example, in the case where multiple SVMs are trained and tested simultaneously with varying kernels, the outputs for each SVM may be compared with output of other SVM to determine the practical optimal solution for that particular set of kernels. The determination of whether an optimal solution has been ascertained may be performed manually or through an automated comparison process.

If it is determined that the optimal minimum has not been achieved by the trained SVM, the method advances to step 224, where the kernel selection is adjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method 200 is repeated from step 208, where the pre-processed training data is input into the SVM for training purposes. When it is determined at step 222 that the optimal minimum has been achieved, the method advances to step 226, where live data is collected similarly as described above. By definition, live data has not been previously evaluated, so that the desired output characteristics that were known with respect to the training data and the test data are not known.

At step 228 the live data is pre-processed in the same manner as was the training data and the test data. At step 230, the live pre-processed data is input into the SVM for processing. The live output of the SVM is received at step 232 and is post-processed at step 234. The method 200 ends at step 236.

Figure 3:
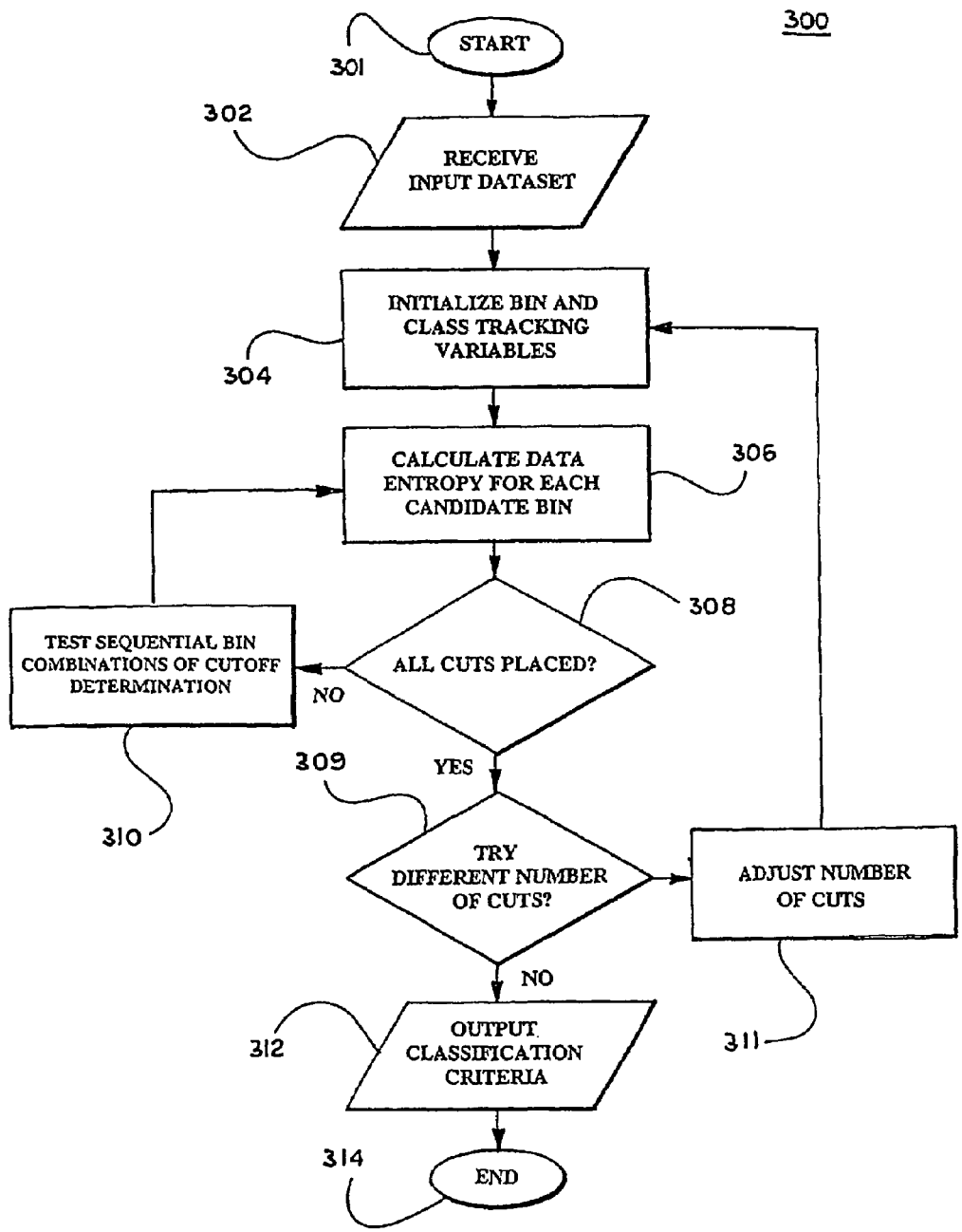
FIG. 3 is a flowchart illustrating an exemplary optimal categorization method that may be used in a stand-alone configuration or in conjunction with a learning machine for pre-processing or post-processing techniques in accordance with an exemplary embodiment of the present invention.

FIG. 3 is a flow chart illustrating an exemplary optimal categorization method 300 that may be used for pre-processing data or post-processing output from a learning machine. Additionally, as will be described below, the exemplary optimal categorization method may be used as a stand-alone categorization technique, independent from learning machines. The exemplary optimal categorization method 300 begins at starting block 301 and progresses to step 302, where an input data set is received. The input data set comprises a sequence of data samples from a continuous variable. The data samples fall within two or more classification categories. Next, at step 304 the bin and class-tracking variables are initialized. As is known in the art, bin variables relate to resolution, while class-tracking variables relate to the number of classifications within the data set. Determining the values for initialization of the bin and class-tracking variables may be performed manually or through an automated process, such as a computer program for analyzing the input data set. At step 306, the data entropy for each bin is calculated. Entropy is a mathematical quantity that measures the uncertainty of a random distribution. In the exemplary method 300, entropy is used to gauge the gradations of the input variable so that maximum classification capability is achieved.

The method 300 produces a series of "cuts" on the continuous variable, such that the continuous variable may be divided into discrete categories. The cuts selected by the exemplary method 300 are optimal in the sense that the average entropy of each resulting discrete category is minimized. At step 308, a determination is made as to whether all cuts have been placed within input data set comprising the continuous variable. If all cuts have not been placed, sequential bin combinations are tested for cutoff determination at step 310. From step 310, the exemplary method 300 loops back through step 306 and returns to step 308 where it is again determined whether all cuts have been placed within input data set comprising the continuous variable. When all cuts have been placed, the entropy for the entire system is evaluated at step 309 and compared to previous results from testing more or fewer cuts. If it cannot be concluded that a minimum entropy state has been determined, then other possible cut selections must be evaluated and the method proceeds to step 311. From step 311 a heretofore untested selection for number of cuts is chosen and the above process is repeated from step 304. When either the limits of the resolution determined by the bin width has been tested or the convergence to a minimum solution has been identified, the optimal classification criteria is output at step 312 and the exemplary optimal categorization method 300 ends at step 314.

The optimal categorization method 300 takes advantage of dynamic programming techniques. As is known in the art, dynamic programming techniques may be used to significantly improve the efficiency of solving certain complex problems through carefully structuring an algorithm to reduce redundant calculations. In the optimal categorization problem, the straightforward approach of exhaustively searching through all possible cuts in the continuous variable data would result in an algorithm of exponential complexity and would render the problem intractable for even moderate sized inputs. By taking advantage of the additive property of the target function, in this problem the average entropy, the problem may be divided into a series of sub-problems. By properly formulating algorithmic sub-structures for solving each sub-problem and storing the solutions of the sub-problems, a significant amount of redundant computation may be identified and avoided. As a result of using the dynamic programming approach, the exemplary optimal categorization method 300 may be implemented as an algorithm having a polynomial complexity, which may be used to solve large sized problems.

As mentioned above, the exemplary optimal categorization method 300 may be used in pre-processing data and/or post-processing the output of a learning machine. For example, as a preprocessing transformation step, the exemplary optimal categorization method 300 may be used to extract classification information from raw data. As a post-processing technique, the exemplary optimal range categorization method may be used to determine the optimal cut-off values for markers objectively based on data, rather than relying on ad hoc approaches. As should be apparent, the exemplary optimal categorization method 300 has applications in pattern recognition, classification, regression problems, etc. The exemplary optimal categorization method 300 may also be used as a stand-alone categorization technique, independent from SVMs and other learning machines.

Figure 4:
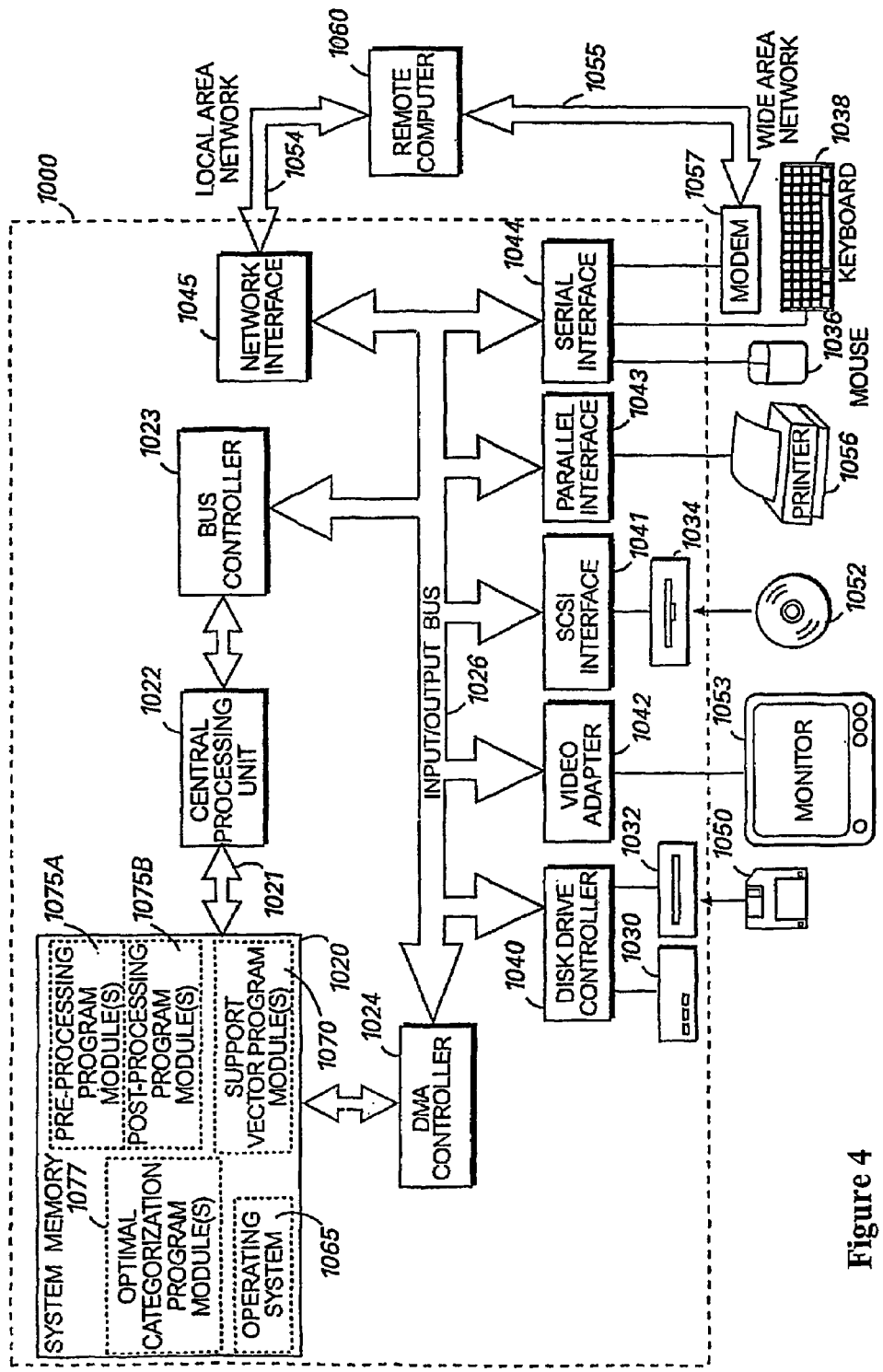
FIG. 4 is a functional block diagram illustrating an exemplary operating environment for an embodiment of the present invention.

FIG. 4 and the following discussion are intended to provide a brief and general description of a suitable computing environment for implementing biological data analysis according to the present invention. Although the system shown in FIG. 4 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described with reference to FIGS. 1 and 2. Furthermore, optimal categorization program modules 1077 may comprise computer-executable instructions for optimally categorizing a data set according to the exemplary methods described with reference to FIG. 3.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 5 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

In another embodiment, a plurality of SVMs can be configured to hierarchically process multiple data sets in parallel or sequentially. In particular, one or more first-level SVMs may be trained and tested to process a first type of data and one or more first-level SVMs can be trained and tested to process a second type of data. Additional types of data may be processed by other first-level SVMs. The output from some or all of the first-level SVMs may be combined in a logical manner to produce an input data set for one or more second-level SVMs. In a similar fashion, output from a plurality of second-level SVMs may be combined in a logical manner to produce input data for one or more third-level SVM. The hierarchy of SVMs may be expanded to any number of levels as may be appropriate. In this manner, lower hierarchical level SVMs may be used to pre-process data that is to be input into higher level SVMs. Also, higher hierarchical level SVMs may be used to post-process data that is output from lower hierarchical level SVMs.

Each SVM in the hierarchy or each hierarchical level of SVMs may be configured with a distinct kernel. For example, SVMs used to process a first type of data may be configured with a first type of kernel while SVMs used to process a second type of data may utilize a second, different type of kernel. In addition, multiple SVMs in the same or different hierarchical level may be configured to process the same type of data using distinct kernels.

Figure 5:
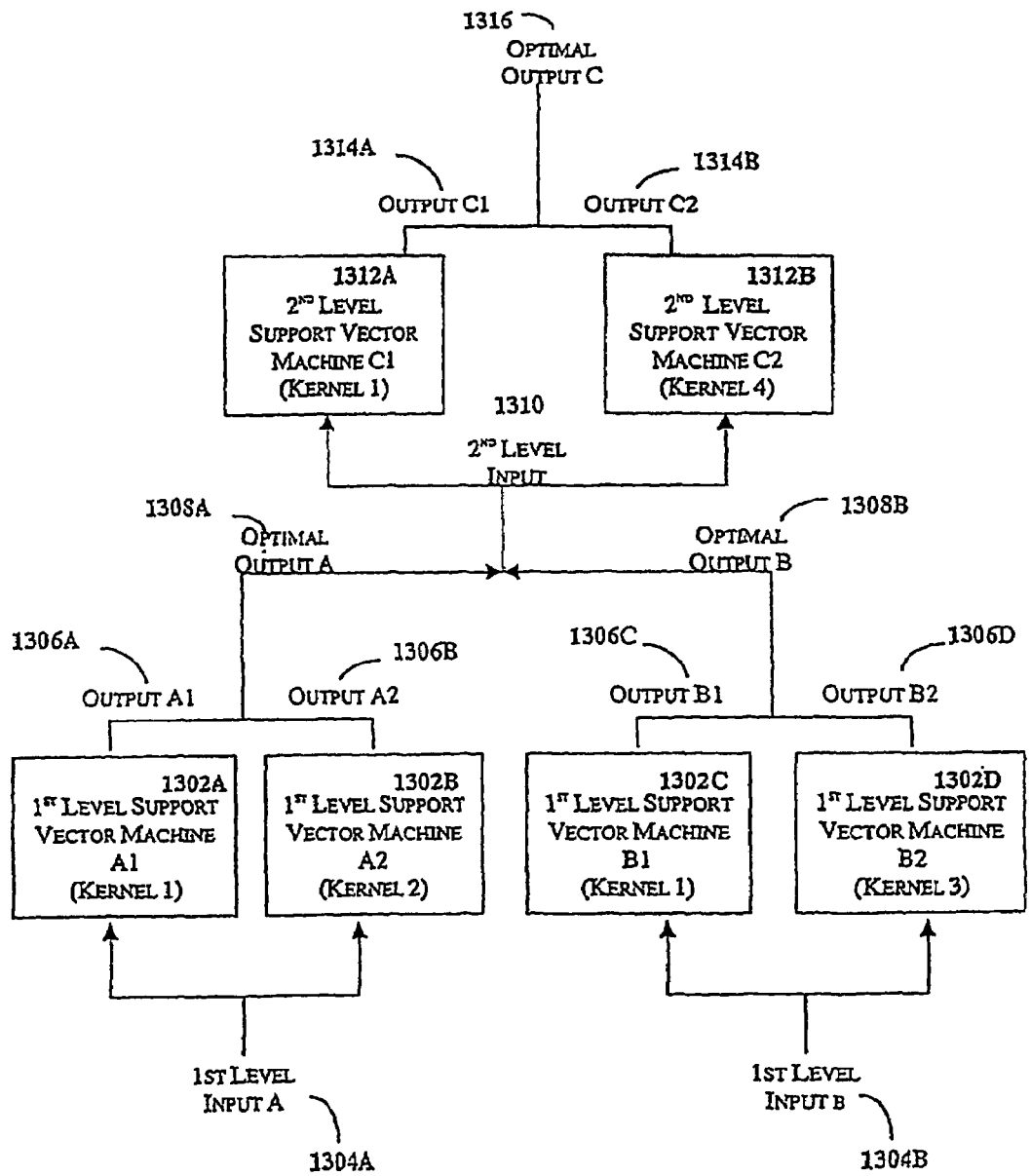
FIG. 5 is a functional block diagram illustrating a hierarchical system of multiple support vector machines.

FIG. 5 illustrates an exemplary hierarchical system of SVMs. As shown, one or more first-level SVMs 1302a and 1302b may be trained and tested to process a first type of input data 1304a, such as mammography data, pertaining to a sample of medical patients. One or more of these SVMs may comprise a distinct kernel, indicated as "KERNEL 1" and "KERNEL 2". Also, one or more additional first-level SVMs 1302c and 1302d may be trained and tested to process a second type of data 1304b, which may be, for example, genomic data for the same or a different sample of medical patients. Again, one or more of the additional SVMs may comprise a distinct kernel, indicated as "KERNEL 1" and "KERNEL 3". The output from each of the like first-level SVMs may be compared with each other, e.g., 1306a compared with 1306b; 1306c compared with 1306d, in order to determine optimal outputs 1308a and 1308b. Then, the optimal outputs from the two groups or first-level SVMs, i.e., outputs 1308a and 1308b, may be combined to form a new multi-dimensional input data set 1310, for example, relating to mammography and genomic data. The new data set may then be processed by one or more appropriately trained and tested second-level SVMs 1312a and 1312b. The resulting outputs 1314a and 1314b from second-level SVMs 1312a and 1312b may be compared to determine an optimal output 1316. Optimal output 1316 may identify causal relationships between the mammography and genomic data points. As should be apparent to those of skill in the art, other combinations of hierarchical SVMs may be used to process either in parallel or serially, data of different types in any field or industry in which analysis of data is desired.

Selection of Kernels

In a first embodiment, a method is provided for construction of kernels for structured data. Specifically, a similarity measure is defined for structured objects in which a location-dependent kernel is defined on one or more structures that comprise patterns in the structured data of a data set. This locational kernel defines a notion of similarity between structures that is relevant to particular locations in the structures. Using the locational kernel, a pair of structures can be viewed as a rich collection of similarities of their components. Multiple locational kernels can then be used to obtain yet another locational kernel. A kernel on the set of structures can be then obtained by combining the locational kernel(s). Different methods for combining the locational kernels include summing the locational kernels over the indices, fixing the indices, and taking the product over all index positions of locational kernels constructed from Gaussian radial basis function (RBF) kernels whose indices have been fixed. The resulting kernels are then used for processing the input data set.

A structured object is represented as a collection of components objects together with their locations within the structure. Given a component set A and α path set P, α structure on A and P is a triple s=(I, c, p), where I is the index set, c :I→A is the component function, and p: I×I→P is the path function. When I is finite, s can be said to be a finite structure.

The index set and component and path functions associated with s are denoted by $I_s$, $c_s$, and $p_s$.

Let S be a set of structures on A and P. A vicinity function for S is α function h:

$$\{(s,i,i'):s \in S, i, i' \in I_s\} \to R \text{ of the form } h(s,i,i')=\phi(p_s(i,i'))$$

for some $\phi: P \to R$.

This vicinity function h is stable if, for all: $s \in S$ and $i \in I_s$, $$\sum_{i' \in I_s} |h(s, i, i')| < \infty. \qquad (2)$$

Notice that every vicinity function on a set of finite structures is stable. The following are a few examples of structures and vicinity functions:

1. If A=R and P=Z, $x \in R^n$ is defined as a finite structure s, where $I_s=\{1, \ldots, n\}$, $c_s(i)=x_i$, and $p_s(i-i')=i-i'$. For example, x might be noisy estimates of the energy in n adjacent frequency bands. In this case, a vicinity function might be defined as $$h(s,i,i')=e^{-c(i-i')^2} \qquad (3)$$

for some c>0. This function models closeness in the frequency domain, since small values of (i–i') correspond to nearby frequency bands.

2. If A is finite alphabet and P=Z, a finite string t on A can be defined as the finite structure s, where $I_s=\{1, \ldots, |t|\}$, with |t| the length of the string t, $c_s(i)=t[i]$, and $p_s(i,i')=i-i'$. For example, t could be a DNA sequence, a protein sequence, or a document, represented as a sequence of words. In such cases, a vicinity function might be defined as $$h(s,i,i')=1(i>i')\lambda^{i-i'} \qquad (4)$$

for some $\lambda \in [0,1)$. For a DNA sequence, one might choose a vicinity function such as $$h(s,i,i')=1(i>i')\lambda_1^{|(i-i'+6 \mod 12)-6|}\lambda_2^{(i-i')} \qquad (5)$$

for some $\lambda_1, \lambda_2 \in [0,1)$. In this case, the vicinity function reflects closeness in the molecule, since elements of the sequence separated by about 12 base pairs are in adjacent coils of the helix.

3. If A=R, P=Z, and $t \in l_2$ is a discrete-time real signal, then one could define the structure s where $I_s=N$, $c_s(i)=t[i]$, and $p_s(i,i')=i-i'$. This is not a finite structure. An example of a vicinity function might be the impulse response $h(s,i,i')=\phi(i-i')$. This leads to some kind of matched filter.

4. If A=[0,1], $P=Z^2$, and $g \in A^{x_s \times y_s}$ is a grayscale image of width $x_s$ pixels and height $y_s$ pixels, then one could define the structure s with $I_s=\{1, \ldots, x_s\} \times \{1, \ldots, y_s\}$, $c_s(x,y)=g[x,y]$, and $$p_s((x,y), (x',y'))=(x-x', y-y') \qquad (6)$$

An example of a vicinity function is $$h(s,(x,y),(x',y'))=e^{-((x-x')^2+(y-y')^2)/(2\sigma^2)} \qquad (7)$$

5. For a directed acyclic graph ("DAG") (V,E) with vertices labeled with elements of A, one could define the structure s with $I_s=V$, component function $c_s(i)$ defined to be the label associated with vertex i, path set P defined as the set of all connected DAGs, and $p_s(i,i')$ is the DAG consisting of all paths from i to i'. For example, A might be a set of part-of-speech tags, and s might correspond to a parse tree, with each vertex labeled with a tag. An example of a vicinity function is $$h(s,i,i')=\lambda^{-d(i,i')}, \qquad (8)$$

where d(i,i') is the number of edges in the shortest directed path from i to i' (or ∞ if there is no such path).

Next, locational kernels are defined to measure the similarity of pairs, e.g., structure or location in the structure. A kernel on a set T means a nonnegative-definite, symmetric, real function on $T^2$.

For concreteness, consider the comparison of two documents, where the documents are represented as sequences of words. The key idea is to construct kernels comparing the two documents centered at particular words, that is, to define a measure of the similarity of two words, surrounded by the rest of the documents.

For a set S of structures, define $$\check{S}=\{(s,i):s \in S, i \in I_s\} \qquad (9)$$

A locational kernel on S corresponds to a kernel on $\check{S}$.

A locational kernel on S is said to be bounded if, for all $s \in I_s$.

$$\max_{i \in I_s} |k((s, i), (s, i))| < \infty \quad (10)$$

Notice that every locational kernel on a set of finite structures is bounded.

If k is a locational kernel on a set S of finite structures, and h is a vicinity function on S. then h*k is a locational kernel on S. This can be shown as follows:

Let $\Phi: \check{S} \to l_2$ be the feature map for k, so that $$k((s, i), (t, j)) = \langle \Phi(s, i), (t, j) \rangle. \quad (11)$$

Then, $$(h*k)((s, i), (t, j)) = \sum_{\substack{i' \in I_s \\ j' \in I_s}} h(s, i, i')h(t, j, j')k((s, i'), \Phi(t, j')) \quad (12)$$

$$= \sum_{i' \in I_s} \sum_{j' \in I_s} h(s, i, i')h(t, j, j')$$

$$\langle \Phi(s, i'), \Phi(t, j') \rangle$$

$$= \left\langle \left(\sum_{i' \in I_s} h(s, i, i')\Phi(s, i')\right), \left(\sum_{j' \in I_s} h(s, j, j')\Phi(t, j')\right) \right\rangle$$

$$= \langle \psi(s, i), \psi(t, j) \rangle,$$

where $$\psi(s, i) = \sum_{i' \in I_s} h(s, i, i')\Phi(s, i').$$

Thus, h*k is a locational kernel on S provided that $\psi$ maps to $l_2$. (See, e.g., Equ. (28).) To see this, notice that $$\|\psi(s, i)\| \leq \sum_{i' \in I_s} \|h(s, i, i')\Phi(s, i')\| \leq \max_{i' \in I_s} \|\Phi(s, i')\| \sum_{i' \in I_s} |h(s, i, i')|, \quad (13)$$

and both factors are finite, since k is bounded and h is stable. The boundedness of k and the stability of h are implied by the finiteness of $I_s$.

Note that the function $((s,i,i'), (t,j,j')) \to h(s,i,i')h(t,j,j')$ is a kernel, and so for the case of finite structures one could express h*k as a special case of an R-convolution.

An interesting class of vicinity functions is obtained by considering smoothness properties of the component function. For example, suppose that $x \in R^n$ is a vector of the energy contained inn band-pass filtered versions of a signal, so that it is a smoothed version of the power of the signal in n adjacent frequency bands. (We can consider x as a structure by defining $A=R'P=Z$, $I_s=\{1, \ldots, n\}$, $c_s(i)=x_i$ and $p_s(i,i')=i-i'$.) Since components of the vector x already contain information about the neighboring components, it might be useful to consider a representation that focuses on how each component deviates from the value implied by a smooth interpolation of the neighboring components. One could, for example, represent each component by the coefficients of a low-degree polynomial that accurately approximates the nearby components, and by the error of such an approximation. In fact, these representations correspond to convolutions of certain vicinity functions with the component kernel.

To see this more generally, consider a kernel $k_0$ on the component space A, and let $\Phi$ be the corresponding feature map from A to $l_2$. Choose some functions $\phi_1, \ldots, \phi_n$ that map from P to R. For each $s \in S$ and $i \in I_s$ define the parameterized map $f: I_s \to l_2$ by $$f_{s,i}(i') = \sum_{n=1}^{N} \alpha_{s,i,n} \phi_n(p_s N(i, i')) \quad (14)$$

for $i' \in I_s$, with parameters $\alpha_{s,i},1, \ldots, \alpha_{s,i,n} \in l_2$. Fix a vicinity function w for S. Then, for each I, these N parameters are chosen to minimize the weighted sum $$\sum_{i' \in I} w(s, i, i') \|f_{s,i}(i') - (\Phi c_s(i'))\|^2, \quad (15)$$

in which case one can loosely think of $f_{s,i}$ as an approximation of $\Phi$ in the vicinity of i.

Also, for these optimal parameters, define $\alpha_{s,i,0} \approx \Phi(c_s(i)) - f_{s,i}(i)$. Then, for each $0 \leq n \leq N$, define the kernel $\check{k}_n((s,i),(t,j)) = \langle \alpha_{s,i,n}, \alpha_{t,j,n} \rangle$.

If the functions $\phi_1, \ldots, \phi_N$ and the weighting function w are such that, for each $s \in S$ and $i \in I_s$ the parameters $\alpha_{s,i,1}, \ldots, \alpha_{s,iN}$ that will minimize Equation (15) are unique, then for any $0 \leq n \leq N$, there is a vicinity function $h_n$ for S for which $\check{k}_n = h_n * k_0$, i.e., $$\langle a_{s,i,n}, a_{t,j,n} \rangle = \sum_{i',j'} h_n(s, i, i')h_n(t, j, j')k_0((s, i'), (t, j')), \quad (16)$$

the proof of which follows:

Fix $s \in$ and $I$. For the objective function $$J = \frac{1}{2} \sum_{i' \in I_s} w(s, i, i') \|f_{s,i}(i') - \Phi(c_s(i'))\|^2, \quad (17)$$

and for $n \in \{1, \ldots, N\}$, the partial derivative of J with respect to the parameter $\alpha_{s,i,n}$ is $$\partial_{a_{s,i,n}} J = \sum_{i' \in I_s} w(s, i, i') \phi_n(p_s(i, i'))(f_{s,i}(i') - \Phi(c_s(i'))). \quad (18)$$

These N partial derivatives are zero when $$\sum_{i' \in I_s} w(s, i, i') \phi_n(p_s(i, i')) \sum_{n=1}^{N} \alpha_{s,i,n} \phi_n(p_s(i, i')) = \quad (19)$$

-continued $$\sum_{i' \in I_s} w(s, i, i')\phi_n(p_s(i, i'))\Phi(c_s(i')) \Leftrightarrow W \begin{pmatrix} a_{s,i,n} \\ \vdots \\ a_{s,i,N} \end{pmatrix} =$$

$$\sum_{i' \in I_s} w(s, i, i')\Phi(c_s(i')) \begin{pmatrix} \phi_1(p_s(i, i')) \\ \vdots \\ \phi_N(p_s(i, i')) \end{pmatrix},$$

where the N×N real matrix W has entries $$W_{n,n'} = \sum_{i' \in I_s} w(s, i, i')\phi_{n'}(p_s(i, i'))\phi_n(p_s(i, i')). \tag{20}$$

If the matrix is invertible, one can write $$a_{s,i,n} = \sum_{i' \in I_s} \Phi(c_s(i'))w(s, i, i') \left[ W^{-1} \begin{pmatrix} \phi_1(p_s(i, i')) \\ \vdots \\ \phi_N(p_s(i, i')) \end{pmatrix} \right]_n \tag{21}$$

$$= \sum_{i' \in I_s} \Phi(c_s(i'))h_n(s, i, i'),$$

where $h_n$ is defined appropriately. This relationship follows for $n=1, \ldots, N$ and the case $n=0$ follows from the definition of $\alpha_{\alpha,s,0}$.

Locational kernels define a notion of similarity between structures s and t that is relevant to particular locations i and j in the structures. For a locational kernel k, $k((s,i), (t,j))$ should be thought of as the similarity of the components of s in the locality of i with the components of t in the locality of j.

If $K_A$ is a kernel on a component set A, and S is a class of structures on A, then one can define a locational kernel on S via $$k((s,i)(t,j)) = K_A(c_s(i), c_t(j)) \tag{22}$$

where s, t∈S, i∈$I_s$, and j∈$I_t$.

Using a locational kernel, two structures s, t∈S can be viewed as a rich collection of similarities of their components. Then, a variety of operations can be performed on locational kernels $k_0, k_1 \ldots$ on S to obtain another locational kernel. For example:

1. Addition:

$$(k_0 + k_1)((s,i),(t,j)) = k_0((s,i),(t,j)) + k_1((s,i),(t,j)) \tag{23}$$

2. Scalar Multiplication: for $\lambda \geq 0$, $$(\lambda k_0)((s,i),(t,j)) = \lambda k_0((s,i),(t,j)) \tag{24}$$

3. Multiplication:

$$(k_0 k_1)((s,i),(t,j)) = k_0((s,i),(t,j))k_1((s,i),(t,j)) \tag{25}$$

4. Pointwise Limits:

$$\left(\lim_{n \to \infty} k_n\right)((s, i), (t, j)) = \lim_{n \to \infty} k_n((s, i), (t, j)) \tag{26}$$

provided the limit exists for all s, t∈S and $I_s$,j∈$I_t$

5. Argument transformations: if T is a set of structures and $f: \check{T} \to \check{S}$, then $$k_f((s,i),(t,j)) = k_0(f(s,i), f(t,j)) \tag{27}$$

is a locational kernel on T. As a special case, if T=S and $I_s = I_t$ for all s, t∈S, one might have $f(s,i) = (f_s(s), f_I(i))$ for some functions $f_s: S \to S$ and $f_I: I_s \to I_s$.

6. Convolution with a Vicinity Function h for S:

$$(h * k_0)((s, i), (t, j)) = \sum_{\substack{i' \in I_s \\ j' \in I_t}} h(s, i, i')h(t, j, j')k_0((s, i'), (t, j')) \tag{28}$$

7. Convolution with a real-valued function v:{(s,t,i,i',j,j'): s, t∈S, i,i'∈$I_s$, j,j'∈$I_t$} →R:

$$(v * k_0)((s, i), (t, j)) = \sum_{\substack{i' \in I_s \\ j' \in I_t}} v(s, t, i, i', j, j')k_0((s, i'), (t, j')) \tag{29}$$

These operations can be combined to obtain, e.g., power series (with nonnegative coefficients) of locational kernels. Moreover, the convolution can be iterated. For example, starting with a kernel $k_A$ on the component set A, $k_0$ can be defined as the corresponding locational kernel on S. The multiplication and convolution operations are iterated as follows. For $n=1, 2, \ldots$, define $$k_n = k_0(h * k_{n-1}), \tag{30}$$

and, with $k'_0 = k''_0$, $$k'_n = k'_{n-1}(h * k_0). \tag{31}$$

Note that $k_1 = k'_1$, and $k'_n = k_0(h*k_0)^n$.

Loosely speaking, $k'_n$ defines the similarity of s at i and t at j as a weighted product of the $k_0$-similarities of n nearby components of s and t, where the weights are given by the product $h(s,i_1,i) \ldots h(s,i_n,i)$. The kernel $k_n$ works in a similar way, but in this case the weights are given by the product $h(s,i_1,i_2) \ldots h(s,i_{n-1},i_n) \cdot h(s,i_n,i)$.

More formally, the following result is obtained:

Let $k_d(\alpha, b) = \langle \Phi(\alpha), \Phi(b) \rangle$ for some feature map $\Phi$: $A \to l_2$, Where $d \in N \cup \{\infty\}$. One can write $$k_n((s,i),(t,i)) = \langle \Psi(s,i), \Psi(t,j) \rangle \tag{32}$$

where $\Psi(s,i)$ is an element of $l_2$ with components $$\Psi(s, i)_{i_1, \ldots, i_n} = \sum_{j_1, \ldots, j_n} \prod_{i=1}^{n} h(s, j_l, j_{l-1})\Phi(c_s(j_l))_{i_l}, \tag{33}$$

where is $i_l \in \{1, \ldots, d\}$. for l=1, \ldots, n, and the sum is over $(j_1, \ldots, j_n) \in I_s^n$, and $j_0 = i$.

Further, $$k'_n((s,i),(t,j)) = \langle \Psi'(s,i), \Psi'(t,j) \rangle, \tag{34}$$

where $\Psi(s,i)$ is an element of $l_2$ with components $$\Psi'(s, i)_{i_1,\ldots,i_n} = \sum_{j_1,\ldots,j_n} \prod_{l=1}^{n} h(s, j_l, i) \Phi(c_s(j_1))_{i_1} \quad (35)$$

where the sum is over $(j_1, \ldots, j_n) \in I_s^n$.

The next step in the process for constructing kernels for structured data is to obtain kernels from the locational kernels. Given a locational kernel, one can obtain a kernel on the set of structures in using a number of different methods.

The first method comprises summing over the indices:

If S is a set of finite structures and k is a locational kernel on S, the kernel K on S can be defined as $$K(s, t) = \sum_{\substack{i \in I_s \\ j \in I_t}} k((s, i), (t, j)) \quad (36)$$

for s, t∈S. More generally, if for every s∈S there is a weighting function $w_s: I_s \to R$, then one can define the kernels K on S as $$K(s, t) = \sum_{\substack{i \in I_s \\ j \in I_t}} w_s(i) w_t(j) k((s, i), (t, j)). \quad (37)$$

If the structures in S are not all finite, but k is bounded and each $w_s$ is absolutely summable, then this definition still gives a kernel. Viewing the kernel as some kind of average of locational kernels looking at the structure's components might yield principled ways of dealing with missing data, i.e., missing components.

Proof of the definition in Equation 37 is as follows: Let $\Phi$: $\check{S} \to l_2$ be the feature map for k, so that $$k((s,i),(t,j)) = \langle \Phi(s,i), \Phi(t,j) \rangle. \quad (38)$$

$$k((s, i), (t, j)) = \langle \Phi(s, i), \Phi(t, j) \rangle. \quad (38)$$

Then, $$K(s, t) = \sum_{i \in I_s, j \in I_t} \sum_{t \in I_s} \sum_{j \in I_t} w_s(i) w_t(j) \langle \Phi(s, i), \Phi(t, j) \rangle \quad (39)$$

$$= \left\langle \left( \sum_{i \in I_s} w_s(i) \Phi(s, i) \right), \left( \sum_{j \in I_t} w_t(j) \Phi(t, j) \right) \right\rangle \quad (40)$$

$$= \langle \psi(s), \psi(t) \rangle, \quad (41)$$

where $$\psi(s) = \sum_{i \in I_s} w_s(i) \Phi(s, i).$$

Thus, K is a kernel on S provided that $\psi$ maps to $l_2$. But $$\|\psi(s)\| \leq \sum_{i \in I_s} \|w_s(i) \Phi(s, i)\| = \max_{i \in I_s} \|\Phi(s, i)\| \sum_{i \in I_s} |w_s(i)|, \quad (42)$$

and both factors are finite. The boundedness of k and the absolute summability of the constant weighting function $w_s(i) \equiv 1$ are implied by the finiteness of $I_s$.

A second method for obtaining the kernel on the set of structures given a location kernel is fixing the indices.

If i is a function on S satisfying $i(s) \in I_s$, then $$K(s,t) = k((s,i(s)),(t,i(t))) \quad (43)$$

is a kernel. Note that one must substitute the same function i in both of k's arguments, to ensure that the result is symmetric in s,t. As a special case, if $I_s = I_t$ for all s,t∈S. one can choose a constant function i.

As a third method, one could use $$K(s,t) = \max k((s,i),(t,j)), \quad (44)$$

to obtain a notion of similarity that is invariant with respect to certain transformations of the index sets (e.g., translations of images), cf. the notion of 'kernel jittering' as discussed by D. DeCoste and M. C. Burl in "Distortion-invariant recognition via jittered queries", *Computer Vision and Pattern Recognition* (*CVPR*-2000), June 2000.

In addition to the foregoing operations, one can apply all known manipulations allowed for kernels. Thus, a wealth of different kernels can be obtained. Further, some 'classical' kernels can be used as special cases:

The Gaussian RBF (radial basis function) kernel is a product (over all index positions) of locational kernels constructed from Gaussian RBF kernels $k_A$ whose indices have been fixed.

a Polynomial kernels of degree n can be obtained via convolutions as follows: consider the case where A=R and $I_s = I_t = I$, use the shorthands $c_s(i) = s_i, c_t(i) = t_i$, and define $$k_0((s,i),(t,j)) = \delta_{ij} \quad (45)$$

as well as, for some real-valued function $u(i,i')$, and $n \in N$, $$k_n((s, i), (t, j)) = \delta_{ij} \sum_{i',j' \in I} s_i u(i, i') t_j u(j, j') k_{n-1}((s, i'), (t, j')). \quad (46)$$

Note that this has the form $k_n = k_0(h * k_{n-1})$, as introduced above, where the vicinity function $h(s,i,i') = s_i u(i,i')$ is used. For constant u, the result is the homogeneous polynomial kernel as shown in the following:

For $n \in N_0$, the vicinity function $h(s,i,i') = s_i$ and the component kernel $k_0(s,i),(t,j)) = \delta_{ij}$ lead to a locational kernel $k_n$, with the property that averaged over all indices, the homogeneous polynomial kernel is recovered.

$$\frac{1}{|I|} \sum_{i,j \in I} k_n((s, i), (t, j)) = \frac{1}{|I|} \sum_{i \in I} k_n((s, i), (t, j)) = \left( \sum_{i \in I} s_i t_i \right)^n. \quad (47)$$

The locational kernel $k_n((s,i),(t,j))$ can thus be thought of as the kernel computing all n-th order product features 'belonging' to index i.

As proof of the preceding, by induction on n, for n=0, Equation 47 holds true. Supposing, then, that it also holds true for n−1, where n≥1, yielding:

$$\frac{1}{|I|}\sum_{i,j\in I} k_n((s,i),(t,j)) = \frac{1}{|I|}\sum_{i,j}\delta_{ij}\sum_{i',j'} s_i t_j k_{n-1}((s,i'),(t,j')) \quad (48)$$

$$= \sum_i s_i t_i \frac{1}{|I|}\sum_{i',j'} k_{n-1}((s,i'),(t,j'))$$

$$= \sum_i s_i t_i \left(\sum_i s_i t_i\right)^{n-1}$$

$$= \left(\sum_i s_i t_i\right)^n.$$

For non-constant functions u, polynomial kernels are obtained where different product features are weighted differently. For example, in the processing of genetic strings, one could use a function u which decays with the distance (on the string) of i and j, e.g., for some c>0, $$u(i,j)=\max\{0, 1-c\cdot|i-j|\}. \quad (49)$$

Thus, one can obtain "locality-improved" kernels such as the ones that have successfully been used in start codon recognition and image processing.

Another interesting generalization of polynomial kernels suggested by the above view is the use of another function instead of $\delta_{ij}$, such as $1_{|i-j|<c}$, for some c∈n. This way, one should obtain polynomial kernels which compare, e.g., sequences that are not precisely registered, thus obtaining some degree of transitional invariance.

$$\langle a_{s,i,n}, a_{t,j,n}\rangle = \sum_{i',j'} h_n(s,i,i') h_n(t,j,j') k_0((s,i'),(t,j)) \quad (50)$$

To provide an example, in the homogeneous polynomial case, where $h(s,i,i')=s_i$, $h(s,j_1,j_{l-1})=h(s,j_1,i)=s_{j-1}$. Therefore, Ψ=Ψ', and thus Equation 47 implies the corresponding result for $k'_n$:

For n∈N₀, $h(s,i,i')=s_i$, and $k_0((s,i),(t,j))=\delta_{ij}$, $$\frac{1}{|I|}\sum_{i,j\in I} k'_n((s,i),(t,j)) = \frac{1}{|I|}\sum_{i\in I} k'_n((s,i),(t,i)) = \left(\sum_{i\in I} s_i t_i\right)^n. \quad (51)$$

Moreover, the component kernel $k_0((s,i),(t,j))=k_A(s_i,t_j)=\delta_{ij}$ can trivially be represented as a dot product in $l_2^d$, where d=|I|, via $\delta_{ij}=\langle e_i,e_j\rangle$, with $\{e_1,\ldots,e_d\}$ an orthonormal basis of $l_2^d$. Therefore, $$\Psi(s,i)_{i_0,\ldots,i_n} = \sum_{j_1,\ldots,j_n} \prod_{l=1}^n s_{j_l}(e_{j_l})_{i_l} \quad (52)$$

$$= \sum_{j_1,\ldots,j_n} \prod_{l=1}^n s_{j_l} \delta_{j_l i_l}$$

$$= \prod_{l=1}^n s_{i_l},$$

the well-known feature map of the homogeneous polynomial kernel, computing all possible products of n components. Note that this is independent of i. Therefore, when summing over all i, the result is a kernel which has the same feature map, up to the overall factor |I|.

Suppose S is the set of finite strings over the finite alphabet A, his defined as $$h(s,i,i')=1(i>i')\lambda^{i-i'} \quad (53)$$

for some λ∈[0,1), and k(α,b)=1(α=b). Then, each component of Φ(α) has the form $$\Phi(\alpha)_i=1(\alpha=\alpha_i), \quad (54)$$

where $A=\{\alpha_1,\ldots,\alpha_{|A|}\}$. In this case, $$k_n((s,i)(t,j))=\langle\Psi(s,i),\Psi(t,j)\rangle, \quad (55)$$

where each component of Ψ(s,i) is of the form $$\Psi(s,i)_{i_0,i_1,\ldots,i_n} = \sum_{i=j_1<\cdots<j_n>i} \lambda^{\sum_{l=1}^n j_l-i} \prod_{l=1}^n \Phi(c_s(j_l))_{i_l} \quad (56)$$

$$= \sum_{i=j_1<\cdots<j_n} \lambda^{\sum_{l=1}^n j_l-i} 1(\forall l, s|j_l| = a_{i_l})$$

That is, the feature space has a component corresponding to each sequence $(\alpha_{i_0},\ldots,\alpha_{i_n})$ and n+1 characters from A, and the value of that component is the sum over all matching subsequences $$(s[i], s[j_1],\ldots, s[j_n])=(\alpha_{i_0},\ldots,\alpha_{i_n}) \quad (57)$$

of λ raised to the power of the length of the gap between the first and last of these characters. This is the string kernel described by H. Lodhi, J. Shawe-Taylor, N. Cristianini, and C. Watkins in "Text classification using string kernels", Technical Report 2000-79, NeuroCOLT, 2000. Published in: T. K. Leen, T. G. Dietterich and V. Tresp (eds.), *Advances in Neural Information Processing Systems* 13, MIT Press, 2001, which is incorporated herein by reference.

Similarly, $$k'_n((s,i),(t,j))=\langle\Psi(s,i),\Psi(t,j)\rangle, \quad (58)$$

Where each component of Ψ(s,i) is of the form $$\Psi(s,i)_{i_0,i_1,\ldots,i_n} = \sum_{j_1,\ldots,j_n>i} \lambda^{\sum_{l=1}^n j_l-i} \sum_{l=1}^n \Phi(c_s(j_l))_{i_l} \quad (59)$$

$$= \sum_{i=j_1,\ldots,j_n>i} \lambda^{\sum_{l=1}^n j_l-i} 1(\forall l, s|j_l| = a_{i_l}).$$

In this case, the value of the component for each sequence $(\alpha i_0,\ldots,\alpha i_n)$ of n+1 characters from A is a sum over all matching, but not necessarily ordered, subsequences (s[i], s[j₁], ... s[jₙ]=(αi₀, ..., αiₙ). For each of these sequences, the component is incremented by λ raised to a power that depends on the distances from i to each matching character. This is a bit like a bag of words approach, in the sense that the characters can appear in any order, but each character's distance from i incurs a penalty. Using another viewpoint, each i,j pair defines the centers of clusters in the two structures, and the value of the locational kernel for those centers is a sum over all sequences of n characters of λ raised to the power of the sum over the sequence of the distances from the character to the center.

The nth order string kernel described by H. Lodhi, et al. can be defined for fixed strings s, t using:

$$K'_0(i, j) = 1 \text{ for all } i, j \text{ and } K'_k(i, j) = 0 \text{ for min}(i, j) < k, \quad (60)$$

$$K'_k(i+1, j) = \lambda K'_k(i, j) + \sum_{j'=1}^{j} 1(s[i+1]$$

$$= t[j'])K'_{k-1}(i, j'-1)\lambda^{j-j'+2},$$

$$K_n(i, j) = 0 \text{ for min}(i, j) < n \quad (61)$$

$$K_n(i+1, j) = K_n(i, j) + \sum_{j'=1}^{j} 1(s[i+1]$$

$$= t[j'])K'_{n-1}(i, j'-1)\lambda^2.$$

Then, the nth order kernel for two strings s, t is defined as $K_n(|s|,|t|)$.

The following result shows that the string kernel is of the form described in Equation 30, with a simple exponential weighting function.

The nth order string kernel of Lodhi et al is given by $$K_n(|s|, |t|) = \lambda^{2n} \sum_{i,j} L_{n-1}(i, j), \quad (62)$$

where, for all integer i, j, $$L_0(i, j) = \begin{cases} 1(s[i] = t[j]) & \text{if } 1 \leq i \leq |s| \text{ and } 1 \leq j \leq |t|, \\ 0 & \text{otherwise} \end{cases} \quad (63)$$

$$L_k(i, j) = L_0(i, j) \sum_{i' \leq i-1} \sum_{j' \leq j-1} \lambda^{(i-1)-i'} \lambda^{(j-1)-j'} L_{k-1}(i', j').$$

This can be proven by first showing by induction that $$L_k(i,j) = \lambda^{-2k} L_0(i,j) K'_k(i-1, j-1) \quad (64)$$

for all i, j, k. (Arbitrary values can be assigned to $K'_k$ when its arguments are outside its range of definition, since $L_0(i, j)$ is zero in that case.) Clearly, Equation 64 is true for k=0 and for all i, j. Suppose it is true for some k≥0, and consider $L_{k+1}$. By Equation 63, $$L_{k+1}(i, j) = L_0(i, j) \sum_{i' \leq i-1} \sum_{j' \leq j-1} \lambda^{(i-1)-i'} \lambda^{(j-1)-j'} L_k(i', j') \quad (65)$$

$$= L_0(i, j) \sum_{i' \leq i-1} \sum_{j' \leq j-1} \lambda^{i-1-i'+j-1-j'-2k} L_0(i', j') K'_k(i'-1, j'-1)$$

$$= \lambda^{-2k-2} L_0(i, j) K'_{k+1}(i-1, j-1).$$

Finally, proving Equation 62, from the definition of $K_n$, it can be shown by induction that $$K_n(i, j) = \lambda^2 \sum_{i'=1}^{i} \sum_{j'=1}^{j} 1(s|i'| = t|j'|) K'_{n-1}(i'-1, j'-1) \quad (66)$$

$$= \lambda^2 \sum_{i'=1}^{i} \sum_{j'=1}^{j} L_0(i', j') K'_{n-1}(i'-1, j'-1)$$

$$= \lambda^{2n} \sum_{i'=1}^{i} \sum_{j'=1}^{j} L_{n-1}(i', j') \text{ by Equation 64.}$$

The above-described locational kernels and method for building on the locational kernels provide a method for defining a kernel similarity measure for general structure objects by comparing the objects centered on individual components thereof. Such kernels and methods may be applied to text documents, DNA sequences, images, time-series data, and spectra, and may be used for analyses including pattern recognition, regression estimation, novelty detection, density estimation and clustering. In applications to biological data, the kernel similarity measure can be used for microarray gene expression measurements, protein measurements and medical images for classification of diseases and disease treatment.

Example 1

Analysis of Spectral Data

The dataset consists of a set of curves coded as vectors of length 1688 and that are described as spectra. The task is to discriminate these spectra from a learning set built of 151 spectra of class 0 and 145 spectra of class 1. Thus, the learning set has a size of 296. The generalization set is not known: it is formed only by the spectra but not by the corresponding labels.

A linear SVM has been trained on the whole learning set. The dataset is linearly separable with a margin of 1.3e-3.

In the experiments, the dataset is used as it is (referred as the "original dataset") or it is normalized (referred as the "normalized dataset"). The normalization consists in subtracting for each spectrum its mean over its coordinates and then to divide all spectra by their own standard deviation.

To deal with this discrimination problem, a linear SVM is applied as follows:

$$\min_{w,b} \|w\|_2^2 + C \sum_{i=1}^{m} \xi_i \text{ subject to: } y_i(\langle w, x_i \rangle + b) \geq -\xi_i \text{ and } \xi_i \geq 0$$

where m=296 is the number of learning points, <.,.> is the dot product, $x_i$ are the spectra of the learning set and $y_i$ are their classes.

The protocol that was used is as follows:
1. Do 100 times:
2. Draw 80% of the learning set and put it in X.
3. Train a linear SVM on the set X.
4. Compute the error on the 20% remaining points of the learning set.
5. Store the error in err.
6. End of Do (1).
7. Output the mean of err over the 100 runs.

Table 1 provides the generalized error rates for normalized and non-normalized data. The number in parenthesis represents the standard deviation.

TABLE 1

| Dataset | C = +∞ | C = 300 |
|---|---|---|
| Normalized dataset | 23.3% (±4.9%) | 22.7% (±5.2%) |
| Non-Normalized dataset | 23.3% (±4.9%) | 25.3% (±4.8%) |

The same experiments were performed with a reduced number of features (the first 543 coordinates of each spectra and the coordinates 1177 to 1500, selected by taking the regions of the graphs that were most different between the two classes 1 and 0), resulting in a generalization error of 22.7% (±5%) with C=∞ on the non-normalized learning set. (The same experiment was not performed with the normalized dataset.)

Another experiment involved splitting the original learning set with all the coordinates into three pieces. The first one (148 spectra) was the set used to define the linear SVM. The second one (59) was used to find the hyperparameter C and the third one (89) was used to test the SVM. The error obtained with a linear SVM on the last set (non-normalized) is 22.5% with C=200. The same experiments with the normalized dataset generated a generalization error of 23.6% with C=20.

Two additional methods were tested:

1) The 1-Nearest Neighbor ("1NN") classifier: the output of this system on a new spectrum is computed by taking the class of the nearest spectrum in the learning set.

2) The Least Min Square ("LMS") classifier: linear whose parameters are obtained with the following optimization problem:

$$\min_{w,b} \sum_{i=1}^{m} (\langle w, x \rangle + b - y_i)^2.$$

The experiments are the same as for the linear SVM. Table 2 shows that, both methods have a greater generalization error than the linear SVM. The number in parenthesis represents the standard deviation.

TABLE 2

| Dataset | 1-NN | LMS |
|---|---|---|
| Normalized dataset | 23.5% (±5.2%) | 27.2% (±5.7%) |
| Non-Normalized dataset | 35.8% (±6.3%) | 28.1% (±9.1%) |

The preliminary results support the fact that this problem may not be solved easily despite the fact that the problem is linearly separable. Non-linear SVM with accurate kernels should be used and a preprocessing step could also be useful. These two steps in the process of setting up a good system require some knowledge on the dataset. It is apparent that the linear system still learns something from this dataset since its error rate is less than 50% (the best solution is 22.5% error rate).

Table 3 sums up the results of the preceding experiments with the results in increasing order. "Norm" indicates that the normalized dataset was used, while "Non-norm" indicates the non-normalized data. "One-run means one run of a SVM whose coefficient C has been defined on a validation set. The latter are presented in decreasing order.

TABLE 3

| Description | Generalization error (std) |
|---|---|
| SVM (C = 200, Non-Norm, one run) | 22.5% |
| SVM (C = 20, Norm, one run) | 23.6% |
| SVM (C = 300, Norm) | 22.7% (±5.2%) |
| SVM (C = ∞, Norm) | 23.3% (±4.9%) |
| SVM (C = ∞, Non-Norm) | 23.3% (±4.9%) |
| 1-NN (Norm) | 23.5% (±5.2%) |
| SVM (C = 300, Non-Norm) | 25.3% (±4.8%) |
| LMS (Norm) | 27.2% (±5.7%) |
| LMS (Non-Norm) | 28.1% (±9.1%) |
| 1-NN (Non-Norm) | 35.8% (±6.3%) |

Next, experiments were performed with non-linear SVMs on the same dataset as in the previous experiments, where the data consists of mid IR spectra of biological samples at 4 wave number resolution. During data collection, care was taken to avoid instrument drifting between the measurements of the two classes. The data are properly labeled and various linear discriminants, including LDA and :partial least square" were used directly on the spectrum used as a feature vector. A feature selection technique was also used.

The kernels used for this series of experiments are the following:

$$k(f, g) = \int f(x)g(x-t)\exp\left(-\frac{t^2}{\sigma}\right)dx\,dt$$

where $f$ and $g$ are spectra. The value of $\sigma$ controls the smoothness of the representation. Experiments were performed for both normalized and non-normalized data.

TABLE 4

| Value of σ | Generalization error (std) | Learning error (std) |
|---|---|---|
| 2.5 | 32.1% (±6.3%) | 23.2% (±5.0%) |
| 5 | 36.3% (±5.5%) | 35.8% (±3.7%) |
| 7.5 | 38.7% (±11.5%) | 35.5% (±10.6%) |
| 10 | 38.8% (±7.6%) | 34.7% (±6.2%) |

The results displayed in Table 4 show that such a kernel does not provide good systems for normalized and non-normalized data. The generalization error is always greater than for linear systems. Smoothness may then appear as a bad property for this particular problem. The fact the learning error is not zero is strong evidence that the smooth representation induced by such kernel is not adapted for this discrimination task. The same experiments were run with a very small $\sigma^1$, producing the same result as for a linear SVM.

Next, the same protocol as for linear SVM previously described was used, but with polynomial kernels:

$$K(f, g) = \left(\frac{\langle f, g \rangle}{1688} + 1\right)^d$$

where d is the degree of the polynomial. All experiments were performed with C=∞. The normalization factor 1/1688 has been used in other experimental settings and has been found to be useful.

The results shown in Tables 5 and 6 are that the learning error for polynomial of degree 1 with C=∞ is not zero. This unusual result may be related to numerical anomalies in the implementation of the SVM software. The best result obtained here is a generalization error of 21.2% with the polynomial of degree 2 such that the improvement from the linear model is not significant.

TABLE 5

| Value of d | Generalization error (std) | Learning error (std) |
|---|---|---|
| 1 | 22.9% (±5.4%) | 4.6% (±4.7%) |
| 2 | 21.2% (±4.7%) | 0.3% (±0.3%) |
| 3 | 22.0% (±5.2%) | 0% (±0%) |
| 4 | 23.4% (±5.1%) | 0% (±0%) |
| 5 | 23.4% (±5.0%) | 0% (±0%) |

TABLE 6

| Value of d | Generalization error (std) | Learning error (std) |
|---|---|---|
| 1 | 23.5% (±5.2%) | 4.2% (±0.9%) |
| 2 | 20.8% (±4.7%) | 0.3% (±0.3%) |
| 3 | 22.6% (±4.7%) | 0% (±0%) |
| 4 | 22.9% (±5.6%) | 0% (±0%) |
| 5 | 22.3% (±4.7%) | 0% (±0%) |

Next, Gaussian kernels were used with $C=\infty$. The kernel used is as $$k(f, g) = \exp\left(\frac{\|f - g\|_2^2}{1688\sigma^2}\right)$$

where $\sigma$ is the standard deviation of the kernel. Results of this experiment are presented in Tables 7 and 8. In order to ensure that an accurate value for $\sigma$ was used, a SVM was run repeatedly for sigma between 0.1 to 10 at increments of 0.1. The best value for $\sigma$ was obtained for $\sigma=1$. Nonetheless, the improvement from the linear model is not significant.

TABLE 7

| Value of $\sigma$ | Generalization error (std) | Learning error (std) |
|---|---|---|
| 0.0001 | 52.9% (±4.4%) | 0% (±0%) |
| 0.001 | 52.1% (±5.1%) | 0% (±0%) |
| 0.01 | 46.7% (±5.5%) | 0% (±0%) |
| 0.1 | 23.3% (±5.5%) | 0% (±0%) |
| 1 | 21.4% (±5.4%) | 0% (±0%) |
| 10 | 22.6% (±5.6%) | 6.5% (±0.9%) |

TABLE 8

| Value of $\sigma$ | Generalization error (std) | Learning error (std) |
|---|---|---|
| 0.0001 | 53.6% (±4.2%) | 0% (±0%) |
| 0.001 | 51.2% (±5.0%) | 0% (±0%) |
| 0.01 | 45.0% (±5.7%) | 0% (±0%) |
| 0.1 | 28.2% (±5.9%) | 0% (±0%) |
| 1 | 21.1% (±5.5%) | 0% (±0%) |
| 10 | 28.7% (±5.2%) | 17.0% (±1.5%) |

According to the nature of the learning problem, it can be useful to use kernels for distribution since a spectrum can be interpreted as the distribution of frequencies. To exploit this, a $\chi^2$ kernel was built as follows:

$$k_\chi(f, g) = \exp(-\chi^2(f, g)) \text{ where } \chi^2(f, g) = \sum_{i=1}^{1688} \frac{(f_i - g_i)^2}{f_i + g_i}$$

Choosing $C=\infty$ and using the same protocol as before, the result is presented in Table 9.

TABLE 9

| | Generalization error (std) | Learning error (std) |
|---|---|---|
| $\chi^2$ kernel (normalized data) | % (±%) | 0% (±0%) |
| $\chi^2$ kernel (non-normalized data) | 40.7% (±6.5%) | 2.1% (±9.5%) |

These results are poor, showing that this kernel, which is not proved to be a Mercer kernel, is not adapted for this task. Many times, the optimization procedure has not converged which indicates that the kernel is not only unacceptable from a learning point of view but also from a computational one.

In these experiments, the representation of the data is changed in which each point of the original curves is replaced by the parameters of a quadratic polynomial that fits the data in a window width 11 centered at the point. More formally, let $f$ be a spectrum, and let $f_i$ be one of its features. Consider the vector $v=(v_i=f_{i-5}, \ldots, v_6=f_i, \ldots, v_{11}=f_{i+5})$ and compute the coefficients of the polyomial $a_i x^2 + b_i x + c_i$ such that:

$$\sum_{j=1}^{11}\left(a_i\left(\frac{j}{11}\right)^2 + b_i\left(\frac{j}{11}\right) + c_1 - v_j\right)^2$$

is minimum. Then, the spectrum is coded as the sequence $(a_i, b_i, c_i, e_i)$ where $$e_i = a_i\left(\frac{6}{11}\right)^2 + b_i\left(\frac{6}{11}\right) + c_i - f_i$$

is the error of the polynomial approximation for $x=i$ which corresponds to $v_6=f_i$. The result of the experiments are described in Table 10. The best result so far is obtained with this representation (19.9% of generalization error). However, this is not significantly different from the result obtained with the same kernel on the normalized dataset (20.8%).

TABLE 10

| Kernel | Generalization error (std) |
|---|---|
| Linear | 26.7% (±5.1%) |
| Polynomial (d = 2) | 22.5% (±5.3%) |
| Polynomial (d = 3) | 20.9% (±5.4%) |
| Polynomial (d = 4) | 20.3% (±5.7%) |
| Polynomial (d = 5) | 19.9% (±5.1%) |
| Polynomial (d = 6) | 20.3% (±5.3%) |
| Polynomial (d = 7) | 20.2% (±4.5%) |
| Polynomial (d = 8) | 20.1% (±4.4) |
| Polynomial (d = 9) | 19.9% (±5.0%) |

Because the above-described method are still far away from the 2% desired error, improved models are explored.

First, each spectrum is coded by the locations of the different maximum. This approach is motivated by the way physicists use a spectrum to analyze the physical properties of a molecule.

Second, data cleaning is used to remove many outliers that make it difficult to generalize.

Figure 6:
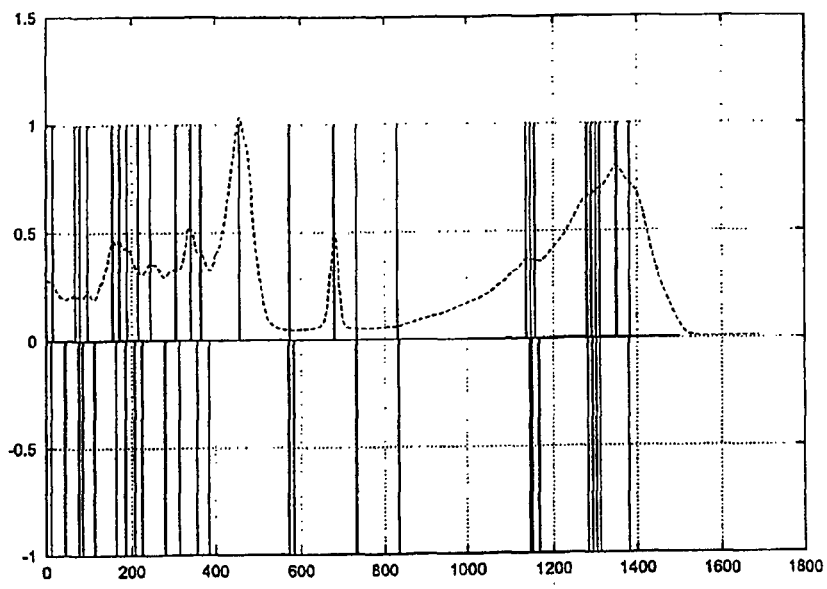
FIG. 6 is a plot showing an original spectra curve superimposed with a new representation of the spectra according to the present invention where the new representation comprises ±1 spikes.

In the first method, the spectra is pre-processed in order to compute the location of their maximum/minimum. Each point in a spectrum that is identified as a maximum (resp. minimum) is affected with a value of +1 (resp. −1). All the other points are set to zero. The hope is that this representation codes the number of maximum/minimum as well as their locations. The latter are usually used by physicists to study such spectra. FIG. 6 illustrates an example of one spectrum, showing the original curve and its new representation as a $\{0,\pm 1\}$-vector, which are represented as $\pm 1$ spikes. Note that there are more extrema coded than can be seen on the curve. This bias is added to avoid loss of information by imposing overly strict conditions for maximum/minimum. Also the last 166 features were removed since they were mainly noise.

The polynomial kernels are normalized by 10, so that:

$$k(f, g) = \left(\frac{\langle f, g \rangle}{10} + 1\right)^d$$

Table 11 provides the results for leave-one-out error for different polynomial kernels with $C=\infty$.

TABLE 11

| Value of the degree d | Leave-one-out error |
| --- | --- |
| 1 | 31.4% |
| 2 | 29.4% |
| 3 | 27.4% |
| 4 | 28.0% |
| 5 | 30.1% |

The normalization number has been chosen in terms of $\langle f,g \rangle$ that is of the order of 10. To compute the maximum and minimum of the spectra, the derivatives of the spectra were first computed, then the position of the zero of these derivatives was identified. The computation of the derivative was done by taking a window of width 5 and by fitting a linear model with bias on this window. The linear part was identified as being the derivative of the spectrum for the point corresponding to the center of the window. The zero elements of the derivative of the spectrum were identified simply by looking at the sign changes.

The results do not provide improvement over the results of earlier tests. However, this does not mean that this kind of approach is not adapted to this problem. Rather, there are many parameters that must be set up in these experiments, including the manners in which the derivative is computed and the extrema are located. Both parameters depend on hand-tuned parameters and can influence the final performance of the model.

Since all of the foregoing models gave roughly the same results for different experimental settings, it appeared that some of the data in the learning set may have been improperly labeled. In order to remove these data, the following data cleaning strategy was used:

1. Do 100 times
2.    Define a random partition of the learning set into two sets: X (80% of the data) and $X_t$ (20% of the data).
3.    Do 100 times,
4.       Define a random partition of X into $X_l$ (60% of the data in X), and $X_v$ (40% of the data in X).
5.       Learn on $X_l$.
6.       Store the error on $X_v$ as a matrix E:

$$E(j) = \begin{cases} \text{Validation error of the i}^{th} \text{ run if j is in } X_l \\ 0 \text{ Otherwise} \end{cases}$$

7.    End For
8.    Compute the mean error = mean (column-wise) of the matrix E.
9.    Order the elements in X with increasing mean error.
10.   Learn the model on the first 80% elements of the ordered set X.
11.   Store the error of the model on $X_t$ in vector err.
12. End Do
13. Output the mean and the standard deviation of err.

The data cleaning step removed 20% of the elements in the sets X (which corresponds to 35 data) before learning the final model. The number 20% was chosen arbitrarily. The experiments were performed with the quadratic representation since it produced the best results thus far. A polynomial kernel of degree 2 was selected, and $C=\infty$ as before. Table 12 summarizes the test error results.

TABLE 12

| Value of the degree d | Generalization error (std) |
| --- | --- |
| 1 | 25.0% (±5.6%) |
| 2 | 21.3% (±4.4%) |
| 3 | 21.1% (±4.7%) |

Once again, the results do not show improvement over earlier methods. However, removing 20% of data from the set X may have been too much and better results could be obtained by removing a smaller percentage of the data. To test this assertion, the same experiment was performed by removing from one to seven data in X. using a linear SVM only. The improvement is not significant.

Rather than learning with all the features, an experiment was performed where seven SVMs trained on different subsets of the features were combined. Actually, seven SVMs were trained on seven segments of the input space. The first SVM concerns the first 251 features, the second concerns the features at position 252-502. The results included a generalization error of 27.5% (±5%) on the original dataset.

A bagging method was applied on the quadratic representation. Fifty splits of the data were computed into a training set of size 251 and a test sets 45. Then, a bagging of 30 SVMs was performed by drawing with replacements 251 points from the training sets according to the uniform distribution over the learning set. For the test set, there was an estimated generalization error of 18% (±5.9%) which represents a slight improvement compared to what has been presented so far.

A different way bagging SVM was tried in which, rather than taking the sign of each single SVM before bagging them, the real output was considered and combined by taking the sign of the sum of their outputs. Also, each single SVM was trained on a set of size 213. The results are shown in Table 13.

TABLE 13

| Representation | Generalization error (std) |
| --- | --- |
| Quadratic (C = ∞) | 20% (±5.2%) |
| Fourier (C = ∞) | 22.4% (±6.7%) |

Finally, the data was split into a learning set (85% of the data) and a test set. Thirty runs of a polynomial SVM (degree 2) were performed on a subset of the training set (80% elements were drawn without replacement in the learning set). The best node was identified by computing its error on the whole learning set, resulting in a generalization error of 19% (±4.2%).

Noise and Invariance. The selection of a kernel corresponds to the choice of representation of the data in a feature space and, to improve performance, it should therefore incorporate prior knowledge such as known transformation invariances or noise distribution. In a second embodiment of kernel selection according to the present invention, an invariance or noise is represented as vectors in a feature space. The noise vectors are taken into account in constructing invariant support vector classifiers to obtain a decision function that is invariant with respect to the noise.

In certain classification tasks, there is a priori knowledge about the invariances related to the task. For example, in image classification, it is known that the label of a given image should not change after a small translation or rotation.

Generally, a local transformation $\mathcal{L}_t$ depending on a parameter t (for instance, a vertical translation of t pixels) is assumed such that any point x should be considered equivalent to $\mathcal{L}_t x$, the transformed point. Ideally, the output of the learned function should be constant when its inputs are transformed by the desired invariance.

It has been shown that one cannot find a non-trivial kernel which is globally invariant (see C. J. C. Burges, "Geometry and invariance in kernel based methods", B. Schölkopf, C. J. C. Burges, and A. J. Smola, editors, *Advances in Kernel Methods—Support Vector* Learning. NIT Press, 1999.) For this reason, local invariances are considered for which each training point $x_i$ is associated with a tangent vector $dx_i$.

$$dx_i = \lim_{t \to 0} \frac{1}{t} (\mathcal{L}_t x_i - x_i) \qquad (67)$$
$$= \frac{\partial}{\partial t}\bigg|_{t=0} \mathcal{L}_t x_i$$

In practice, $dx_i$ can be either computed by finite difference or by differentiation. Note that generally one can consider more than one invariance transformation. The multi invariance case is usually a straightforward extension of the single one.

A common method for introducing invariances in a learning system is to add the perturbed examples $\mathcal{L}_t x_i$ in the training set (see P. Niyogi, T. Poggio, and F. Girosi, "Incorporating prior information in machine learning by creating virtual examples", *IEEE Proceedings on Intelligent Signal Processing*, 86(11):2196-2209, November 1998). These points are often labeled "virtual examples". In the SVM (support vector machine) framework, when applied only to the SVs (support vectors), it leads to the "Virtual Support Vector" ("VSV") method. See, e.g., B. Schölkopf, C. Burges, and V. Vapnik. "Incorporating invariances in support vector learning machines", *Artificial Neural Networks—ICANN'96*, volume 1112, pages 47-52, Berlin, 1996. Springer Lecture Notes in Computer Science.

An alternative to the foregoing is to directly modify the cost function in order to take into account the tangent vectors. This has been successfully applied to neural networks (P. Simard, Y. LeCun, J. Denker, and B. Victorri. "Transformation invariance in pattern recognition, tangent distance and tangent propagation", G. Orr and K. Müller, editors, *Neural Networks: Tricks of the Trade*. Springer, 1998.) and linear Support Vector Machines (B. Schölkopf, P. Y. Simard, A. J. Smola, and V. N. Vapnik. Prior knowledge in support vector kernels. In MIT Press, editor, NIPS, volume 10, 1998), both of which are incorporated herein by reference. According to the present embodiment of the invention, such methods are extended to the case of nonlinear SVMs, primarily by using kernel PCA (principal components analysis) methods. See, e.g., B. Schölkopf, A. Smola, and K. R. Müller. Nonlinear component analysis as a kernel eigenvatue problem. *Neural Computation*, 10:1299-1310, 1998, which is incorporated herein by reference.

The following description provides a few of the standard notations used for SVMs. Let $\{(x_i,y_i)\}1<n$ be a set of training examples, $x_i \dot{\in} \mathcal{X}$ belonging to classes labeled by $y_i \dot{\in} \{-1,1\}$. The domain $\mathcal{X}$ is often, but not necessarily, taken to be $\mathbb{R}^d$, $d \in \mathbb{N}$. In kernel methods, these vectors are mapped into a feature space using a kernel function $K(x_i,x_j)$ that defines an inner product in this feature space. The decision function given by an SVM is the maximal margin hyperplane in this space, $$g(x) = \text{sign}(f(x)), \text{ where } f(x) = \left(\sum_{i=1}^{n} \alpha_i^0 y_i K(x_i, x) + b\right). \qquad (68)$$

The coefficients $a_i^0$ are obtained by maximizing the functional $$W(\alpha) = \sum_{i=1}^{n} \alpha_i - \frac{1}{2} \sum_{i,j=1}^{n} \alpha_i \alpha_j y_i y_j K(x_i, x_j) \qquad (69)$$

under the constraints $$\sum_{i=1}^{n} \alpha_i y_i = 0 \text{ and } \alpha_i \geq 0.$$

This formulation of the SVM optimization problem is referred to as the "hard margin" formulation since no training errors are allowed. Every training point satisfies the inequality $y_i f(x_i) \geq 1$; points $x_i$ with $\alpha_i > 0$ satisfy it as an equality. These points are called "support vectors."

For the non-separable case, training errors must be permitted, which results in the so-called "soft margin" SVM algorithm (see C. Cortes and V. Vapnik, "Support vector networks", *Machine Learning*, 20:273-297, 1995). It can be shown that soft margin SVMs with quadratic penalization of errors can be considered as a special case of the hard margin version with the modified kernel (N. Cristianini and J. Shawe-Taylor, *An Introduction to Support Vector Machines*. Cambridge University Press, 2000).

$$K \leftarrow K + \frac{1}{C}I, \tag{70}$$

where I is the identity matrix and C a parameter penalizing the training errors. However, the primary focus of the present invention is on the hard margin SVM.

For linear SVMs, one wishes to find a hyperplane whose normal vector w is as orthogonal as possible to the tangent vectors. This can be. readily understood from the equality $$f(x_i + dx_i) - f(x_i) = w \cdot dx_i.$$

For this purpose, it has been suggested to minimize the functional $$(1-\gamma)w^2 + \gamma \sum_{i=1}^{n}(w \cdot dx_i)^2 \tag{71}$$

subject to the constraints $$\gamma_i(w \cdot x_i + b) \geq 1.$$

The parameter γ trades off between normal SVM training (γ=0) and full enforcement of the orthogonality between the hyperplane and the invariance directions (γ→1).

The square root of the regularized covariance matrix of the tangent vectors is:

$$C_\gamma = \left((1-\gamma)I + \gamma \sum_i dx_i dx_i^T\right)^{1/2}, \tag{72}$$

where τ indicates the transpose.

Equation 71 then reads $$w^\tau C_\gamma^2 w.$$

Introducing $\tilde{w} = C_\gamma w$ and $\tilde{x}_i = C_\gamma^{-1} x_i$, the equivalent optimization problem is:

$$\min_{\tilde{w}} \tilde{w}^2 \tag{73}$$

under constraints $$\gamma_i(\tilde{w} \cdot \tilde{x}_i + b) \geq 1.$$

The preceding makes use of the equality $C_\gamma^{-1} w \cdot x_i = w \cdot C_\gamma^{-1} x_i$, which is valid because $C_\gamma$ is symmetric. Note also that $C_\gamma$ is strictly positive definite (and thus invertible) if γ<1. For this reason, for the remainder of this description, it will be assumed that γ<1.

The optimization problem of Equation (73) is the standard SVM situation where the training points $x_i$ have been linearly pre-processed using the matrix $C_\gamma^{-1}$.

The output value of the decision function on a test point is:

$$f(x) = w \cdot x_i + b \tag{74}$$

$$= \tilde{w} \cdot C_\gamma^{-1} x + b - \sum_{i=1}^{n} \alpha_i y_i C_\gamma^{-1} x_i \cdot C_\gamma^{-1} x + b$$

The standard formulation of an SVM output is also obtained, however, the test point is first multiplied by $C_\gamma^{-1}$.

To conclude, it can be said that a linear invariant SVM is equivalent to a standard SVM where the input space has been transformed through the linear mapping $$x \to C_\gamma^{-1} x \tag{75}$$

It has been shown that this method leads to significant improvements in linear SVMs, and to small improvements when used as a linear preprocessing step in nonlinear SVMs. The latter, however, was a hybrid system with unclear theoretical foundations. The following description provides a method for dealing with the nonlinear case in a principled way.

In the nonlinear case, the data are first mapped into a high-dimensional feature space where a linear decision boundary is computed. To extend the previous analysis to the nonlinear case, one would need to compute the matrix $C_\gamma$ in feature space, $$C_\gamma = \left((1-\gamma)I + \gamma \sum_i d\Phi(x_i) d\Phi(x_i)^T\right) \tag{76}$$

and the new kernel function $$\tilde{K}(x,y) = C_\gamma^{-1}\Phi(x) \cdot C_\gamma^{-1}\Phi(y) = \Phi(x)^\tau C_\gamma^{-2} \Phi(y) \tag{77}$$

However, due to the high dimension of the feature space, it is not practical to do it directly. There are two different techniques for overcoming this difficulty, however, the "kernel PCA map" must first be introduced.

Even in the case of a high dimensional feature space $\mathcal{H}$ a training set $(x_1, \ldots, x_n)$ of size n when mapped to this feature space spans a subspace $E \subset \mathcal{H}$. whose dimension is at most n. The "kernel PCA map", described by Schölkopf, Smola and Müller (supra) and extended in K. Tsuda, "Support vector classifier with asymmetric kernel function", In M. Verleysen, editor, *Proceedings of ESANN'99*, pages 183-188, 1999, incorporated herein by reference, makes use of this idea.

Let $(v_1, \ldots, v_n) \in E^n$ be an orthonormal basis of E with each $v_i$ being a principal axis of $\{\Phi(x_1), \ldots, \Phi(x_n)\}$. The kernel PCA map ψ: X→$R^n$ is defined coordinatewise as $$\psi_p(x) = \Phi(x) \cdot v_p, 1 \leq p \leq n \tag{78}$$

Note that by definition, for all i and j, $\Phi(x_i)$ and $\Phi(x_j)$ lie in E and thus $$K(x_i, x_j) = \Phi(x_i) \cdot \Phi(x_j) = \psi(x_i) \cdot \psi(x_j). \tag{79}$$

Equation 79 reflects the fact that if all principal components are retained, kernel PCA is merely a basis transform in E, leaving the dot product of training points invariant.

In the decomposition of the principal directions $(v_1, \ldots, v_n)$, for $1 \leq p \leq n$, $v_p$ can be written as $$v_p = \sum_{i=1}^{n} a_{ip} \Phi(x_i). \qquad (80)$$

The fact that $(v_i, \ldots, v_n)$ are the principal directions in feature space of the training set means that they are eigenvectors of the covariance matrix, $$Cv_p = \lambda_p v_p, \ 1 \leq p \leq n \qquad (81)$$

where $$C = \sum_{i=1}^{n} \Phi(x_i) \Phi(x_i)^T. \qquad (82)$$

Note that it is assumed that the data are centered in feature space. It is actually always possible to center the data. See, e.g., Schölkopf, Smola and Müller (supra) for details on how this may be accomplished.

Combining Equations (80), (81) and (82), and multiplying the left side by $\Phi(x_k)^\tau$, yields $$\Phi(x_k)^T \left( \sum_{i=1}^{n} \Phi(x_i) \Phi(x_i)^T \right) \sum_{j=1}^{n} a_{jp} \Phi(x_j) = \lambda_p \Phi(x_k)^T \sum_{j=1}^{n} a_{jp} \Phi(x_j), \qquad (83)$$

which can be written as $$\sum_{i,j=1}^{n} K(x_i, x_k) K(x_i, x_j) a_{jp} = \lambda_p \sum_{j=1}^{n} a_{jp} K(x_k, x_j), \ 1 \leq p, k \leq n. \qquad (84)$$

In matrix notation, this last equality reads $$K^2 \alpha_p = \lambda_p \alpha_p$$

which is satisfied whenever $$K\alpha_p = \lambda_p K\alpha_p. \qquad (85)$$

Thus, if $\alpha_p$ is an eigenvector of the kernel matrix K, its components can be used in the Equation 80. Note that the eigenvalues of K are the same as those in the covariance matrix of Equation 82.

Enforcing the constraint that $v_p$ has unit length, Equations 80 and 85 yield $$v_p^2 = \alpha_p^\tau K \alpha_p = \lambda_p \alpha_p^2. \qquad (86)$$

Writing the eigendecomposition of K as $$K = U \Lambda U^\tau, \qquad (87)$$

with U being an orthonormal matrix and $\Lambda$ a diagonal matrix, $a_{ip} = U_{ip}/\sqrt{\lambda_p}$, so the kernel PCA map reads $$\psi(x) = \Lambda^{-1/2} U^\tau k(x) \qquad (88)$$

where $$k(x) = (K(x, x_1), \ldots, K(x, x_n))^\tau. \qquad (89)$$

In order to be able to compute the new kernel according to Equation 77, the matrix $C_\gamma$ (Equation 76) is diagonalized using the same approach as that described in the preceding section. In that section, it was shown to diagonalize the feature space covariance matrix in the PCA subspace (spanned by a training sample) by computing the eigendecomposition of the Gram matrix of those points. Now, rather than having a set of training points $\{\Phi(x_i)\}$, there is given a set of tangent vectors $\{d\Phi(x_i)\}$ and a tangent covariance matrix $$C^t = \sum_{i=1}^{n} d\Phi(x_i) d\Phi(x_i)^T. \qquad (90)$$

Considering the Gram matrix $K^t$ of the tangent vectors:

$$\begin{aligned} K_{ij}^t &= d\Phi(x_i) \cdot d\Phi(x_j) \qquad (91) \\ &= K(x_i + dx_i, x_j + dx_j) - K(x_i + dx_i, x_j) - \\ &\quad K(x_i, x_j + dx_j) + K(x_i, x_j) \\ &= dx_i^T \frac{\partial^2 K(x_i, x_j)}{\partial x_i \partial x_j} dx_j \qquad (92) \end{aligned}$$

This matrix $K^t$ can be computed either by finite differences (Equation 91) or with the analytical derivative expression given by Equation 92. Note that for a linear kernel, $K(x, y) = x^\tau y$, and (17) reads $K_{ij}^t = dx_i^\tau dx_j$, which is a standard dot product between the tangent vectors.

As in the foregoing description of the kernel PCA map, the eigendecomposition of $K^t$ is written as $K^t = U \Lambda U^\tau$, which allows the expansion of the eigenvectors $(v_1, \ldots, v_n)$ of $C^t$ corresponding to non-zero eigenvalues to be found.

$$v_p = \frac{1}{\sqrt{\lambda_p}} \sum_{i=1}^{n} U_{ip} d\Phi(x_i). \qquad (93)$$

The orthonormal family $(v_1, \ldots, v_n)$ to an orthonormal basis of $\mathcal{H}(v_1, \ldots, v_n, v_n+1, \ldots, v_{d\mathcal{H}})$ is completed, with $d\mathcal{H} = \dim \mathcal{H} \leq \infty$.

In this basis, $C^t$ is diagonal $$C^t = VD(\lambda_1, \ldots, \lambda_n, 0, \ldots, 0)V^\tau,$$

where V is an orthonormal matrix whose columns are the $v_i$. Referring back to Equation 77 the matrix of interest is $C_\gamma^{-2}$ $$C_\gamma^{-2} = VD\left(\frac{1}{\gamma \lambda_1 + 1 - \gamma}, \ldots, \frac{1}{\gamma \lambda_n + 1 - \gamma}, \frac{1}{1 - \gamma}, \ldots, \frac{1}{1 - \gamma}\right) V^T, \qquad (94)$$

To be able to compute the new kernel function according to Equation 77, the projection of a point in feature space $\Phi(x_i)$ onto one of the vectors $v_p$ must be determined. From Equation 93, we have, for $1 \leq p \leq n$, $$\Phi(x) \cdot v_p = \frac{1}{\sqrt{\lambda_p}} \sum_{i=1}^{n} U_{ip}(K(x_i + dx_i, x) - K(x_i, x)) \quad (95)$$

$$= \frac{1}{\sqrt{\lambda_p}} \sum_{i=1}^{n} U_{ip} dx_i^T \frac{\partial K(x_i, x)}{\partial x_i}.$$

For p>n, however, the dot product $\Phi(x) \cdot v_p$ is unknown. Therefore, Equation 77 must be rewritten as $$\tilde{K}(x, y) = \Phi(x)^T \left( C_\gamma^{-2} - \frac{1}{1-\gamma} I \right) \Phi(y) + \frac{1}{1-\gamma} K(x, y) \quad (96)$$

From Equation 94, it can be seen that the eigenvalues of $$C_\gamma^{-2} - \frac{1}{1-\gamma} I$$

associated with the eigenvectors $v_p$ are zero for p>n.

Combining Equations 94, 95 and 96 produces $$\tilde{K}(x, y) = \frac{1}{1-\gamma} K(x, y) + \quad (97)$$

$$\sum_{p=1}^{n} \Phi(x) \cdot v_p \left( \frac{1}{\gamma \lambda_p + 1 - \gamma} - \frac{1}{1-\gamma} \right) \Phi(y) \cdot v_p$$

$$= \frac{1}{1-\gamma} K(x, y) + \sum_{p=1}^{n} \frac{1}{\gamma_p} \left( \frac{1}{\gamma \lambda_p + 1 - \gamma} - \frac{1}{1-\gamma} \right)$$

$$\left( \sum_{i=1}^{n} U_{ip} dx_i^T \frac{\partial K(x_i, x)}{\partial x_i} \right) \left( \sum_{i=1}^{n} U_{ip} dx_i^T \frac{\partial K(x_i, y)}{\partial x_i} \right)$$

One drawback of the previous approach appears when dealing with multiple invariances (i.e., more than one tangent vector per training point). Under such conditions, one must diagonalize the matrix $K^t$ (see Equation 91) whose size is equal to the number of invariances.

To introduce multiple invariances, an alternative method can be used which consists of decomposing the Gram matrix of the input vectors. This technique uses the PCA kernel map described above. In that method, a training sample of size n spans a subspace E whose dimension is at most n. The empirical kernel map $\psi$ (see Equation 88) gives in an orthonormal basis the components of a point $\Phi(x)$ projected on E.

From Equation 79, it is can be seen that training a nonlinear SVM on $\{x_1, \ldots, x_n\}$ is equivalent to training a linear SVM on $\{\psi(x_1), \ldots, \psi(x_n)\}$ and thus, due to the nonlinear mapping $\psi$, one can work directly in the linear space E and use the same technique described above for invariant linear SVMs (see Equations 71-73). However, the invariance direction $d\Phi(x_i)$ does not necessarily belong to E. By projecting them onto E, some information might be lost. However, this approximation gives a similar decision function to that obtained using decomposition of the Gram matrix of the tangent vectors.

Finally, the proposed algorithm consists of training an invariant linear SVM as previously described for invariant linear SVMs with training set $\{\Psi(x_1), \ldots, \Psi(x_n)\}$ and with invariance directions $\{d\Psi(x_1), \ldots, d\Psi(x_n)\}$, where $$d\psi(x_i) = \psi(x_i + dx_i) - \psi(x_i), \quad (98)$$

which can be expressed from Equation 88 as $$d\psi(x_i)_p = \frac{dx_i^T}{\sqrt{\lambda_p}} \sum_{j=1}^{n} U_{jp} \frac{\partial K(x_i, x_j)}{\partial x_i}. \quad (99)$$

It is possible to estimate how much information has been lost by projecting $d\Phi(x_i)$ on E with the ratio $$\frac{\|d\psi(x_i)\|}{\|d\Phi(x_i)\|} \leq 1 \quad (100)$$

The techniques of enforcing an invariance and adding the virtual examples $\mathcal{L}_i x_i$ in the training set are related and some equivalence can be shown (see Todd K. Leen, "From data distributions to regularization in invariant learning", *Nips*, volume 7. The MIT Press, 1995), however, there are some differences.

When using the Virtual Support Vector (VSV) method, if a training point $x_i$ is far from the margin, adding the virtual example $\mathcal{L}_i x_i$ will not change the decision boundary since neither of the points can become a support vector. Hence, adding virtual examples in the SVM framework enforces invariance only around the decision boundary, which is the main reason that the virtual SV method only adds virtual examples generated from points that were support vectors in the earlier iteration.

It might be argued that the points that are far from the decision boundary do not provide any significant information. On the other hand, there is some merit in not only keeping the output label invariant under the transformation $\mathcal{L}_i$ but also the real-valued output. This can be justified by interpreting the distance of a given point to the margin as an indication of its class-conditional probability (see John Platt, "Probabilities for support vector machines", A. Smola, P. Bartlett, B. Schölkopf, and D. Scbuurmans, editors, *Advances in Large Margin Classifiers*. MIT Press, Cambridge, Mass., 2000). It appears reasonable that an invariance transformation should not affect this probability too much.

Figure 7:
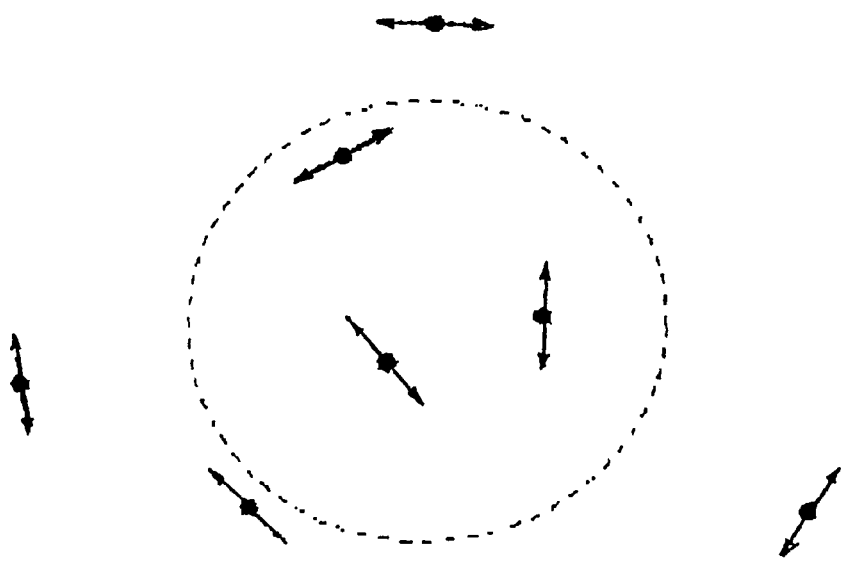
FIG. 7 illustrates a toy problem where the true decision function is the circle. For each point a tangent vector corresponding to a small rotation is plotted.

This advantage can be illustrated using the Example toy picture of FIG. 7. Referring to the bottom right corner of the figure, the point might not be a support vector, however, it is still worth enforcing that the level curves around that point follow the direction given by its tangent vector.

The complexity of computing the kernel PCA map $\Psi(x)$ (Equation 88) is of the order $n^2$: E is an n-dimensional space and each basis vector is expressed as a combination of n training points (see also Equation 93). There are, thus, two ways of reducing the complexity:

1. Reduce the dimension of E by keeping only the leading principal components; and
2. Express each basis vector $v_p$ as a sparse linear combination of the training points.

Additional details can be obtained from C. Williams and M. Seeger., "Using the Nystrom method to speed up kernel machines", *Advances in Neural Information Processing Systems* 13, pages 682-688. MIT Press, 2001.

A straightforward way to reduce the complexity is based on the method consisting of decomposition of the Gram matrix of the input vector described above. Here, a random subset of the training points of size m<<n is selected. Work is performed in the subspace E' spanned by those m points. In practice, this means that the kernel PCA map (Equation 88) can be computed only from the m training examples. However, there is a loss of information by projecting on E' instead of E, but if the eigenvalues of the kernel function decay quickly enough and m is large enough, $\|P_E(x)-P_{E'}(x)\|$ should be small, where P is the projection operator. (See A. J. Smola and B. Schölkopf, "Sparse greedy matrix approximation for machine learning", P. Langley, editor, *Proceedings of the 17th International Conference on Machine Learning*, pages 911-918, San Francisco, 2000. Morgan Kaufman.)

The method using the Gram matrix of the tangent vectors (Equations 90-95) described above amounts to finding the linear invariant hyperplane in the subspace spanned by the tangent vectors (in feature space). The method using the Gram matrix of the input vectors (training points) amounts to doing the same thing, but in the subspace spanned by the training points. More generally, one could consider an hybrid method where the linear invariant hyperplane is constructed in the linear space spanned by a subset of the tangent vectors and a subset of the training points.

EXAMPLES

In the following examples, a standard SVM is compared with several methods taking into account invariances:

Standard SVM with virtual example (VSV).

Invariant SVM as described in above (ISVM).

Invariant hyperplane in kernel PCA coordinates as described above ($IH_{KPCA}$).

SVM trained with points pre-processed through the linear invariant hyperplane method (LIH)

The last method refers to disclosure provided by Schölkopf, Simard Smola and Vapnik (supra) where the authors describe the invariant linear SVM. In the following examples, the training and test points were linearly pre-processed using $C_\gamma^{-1}$ (Equation 73). Afterwards, instead of training a linear SVM, a nonlinear SVM was trained. Even though there is no guarantee that such an approach will work, experimental results on the NIST Rational Institute of Standards and Technology) set showed a slight improvement over the standard nonlinear SVM. The examples include tests run on a toy problem and a digit recognition dataset.

In all methods described for training an invariant SVM, there is a parameter γ that must be chosen, which is a trade-off between maximization of the margin and enforcement of the invariances (see, e.g., Equation 71). One can set this parameter using a validation set or by gradient descent. (O. Chapelle, V. Vapnik, V. Bousquet, and S. Mukherjee, "Choosing multiple parameters for support vector machines", *Machine Learning*, 2001.)

In order to have a functional which is scale invariant with respect to the size of $dx_i$ (in other words, the parameterization of $\mathcal{L}_i$, instead of minimizing the functional of Equation 71, the following is minimized:

$$(1-\gamma)w^2 + \gamma \sum_{i=1}^{n} \frac{(w \cdot dx_i)^2}{S}, \qquad (101)$$

with $$S = \sum_{i=1}^{n} dx_i^2.$$

This is equivalent to minimizing the functional of Equation 71 where γ is replaced by $$\gamma \leftarrow \frac{\gamma}{S + \gamma(1-S)}. \qquad (102)$$

Example 2

Toy Problem

Referring to FIG. 7, the toy problem is as follows: the training data has been generated uniformly from $[-1,1]^2$. The[.] true decision boundary is a circle centered at the origin:

$$f(x)=\text{sign}(x^2-0.7). \qquad (103)$$

The a priori knowledge to be encoded in this toy problem is local invariance under rotations. Therefore, the output of the decision function on a given training point $x_i$ and on its image $R(x_i,\epsilon)$ obtained by a small rotation should be as similar as possible. To each training point, a tangent vector $dx_i$ is associated which is actually orthogonal to $x_i$.

A training set of 30 points was generated and the experiments were repeated 100 times. A Gaussian kernel $$K(x, y) = \exp\left(\frac{\|x-y\|^2}{2\sigma^2}\right) \qquad (104)$$

was chosen.

Figure 8A:
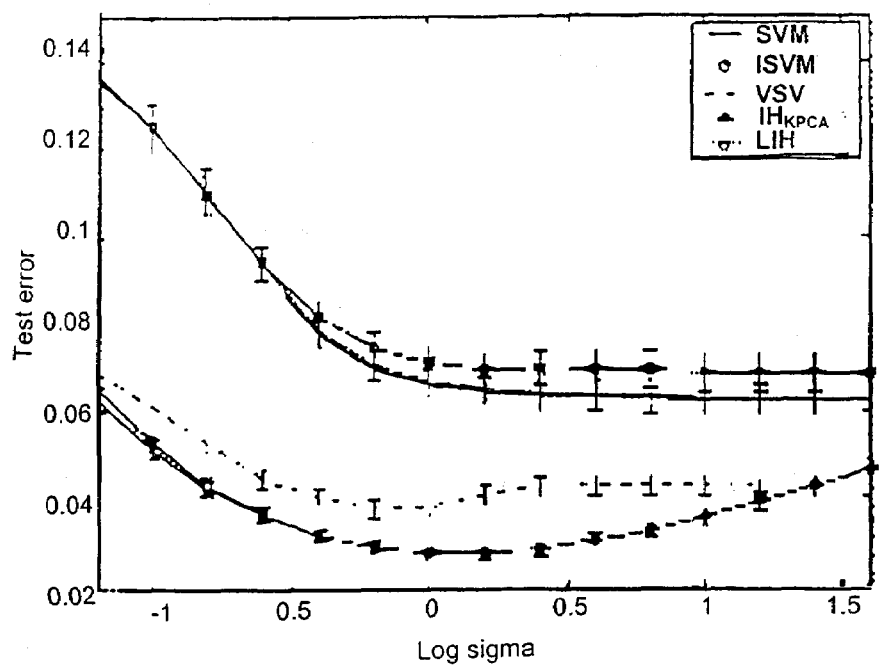
FIGS. 8a and b are plot showing test errors where
Figure 8B:
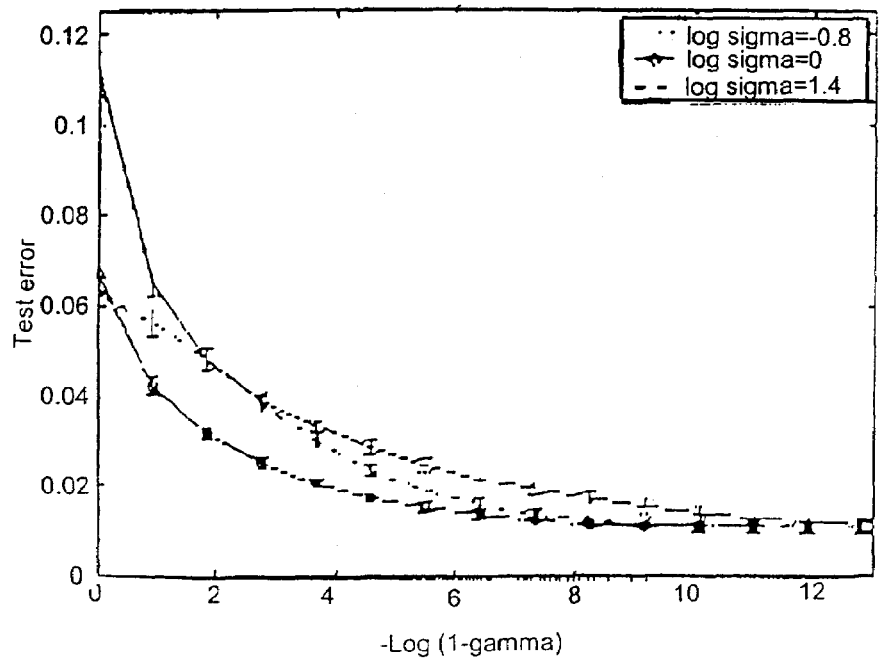
FIG. 8b represents test error of $IH_{KPCA}$ across $\tau$ and for different values of $\sigma$. The test errors are averaged over the 100 splits and the error bars correspond to the standard deviation of the means.

The results are summarized in FIGS. 8a and 8b, with the following observations:

For each σ, adding virtual training examples reduces the test error.

Figure 9:
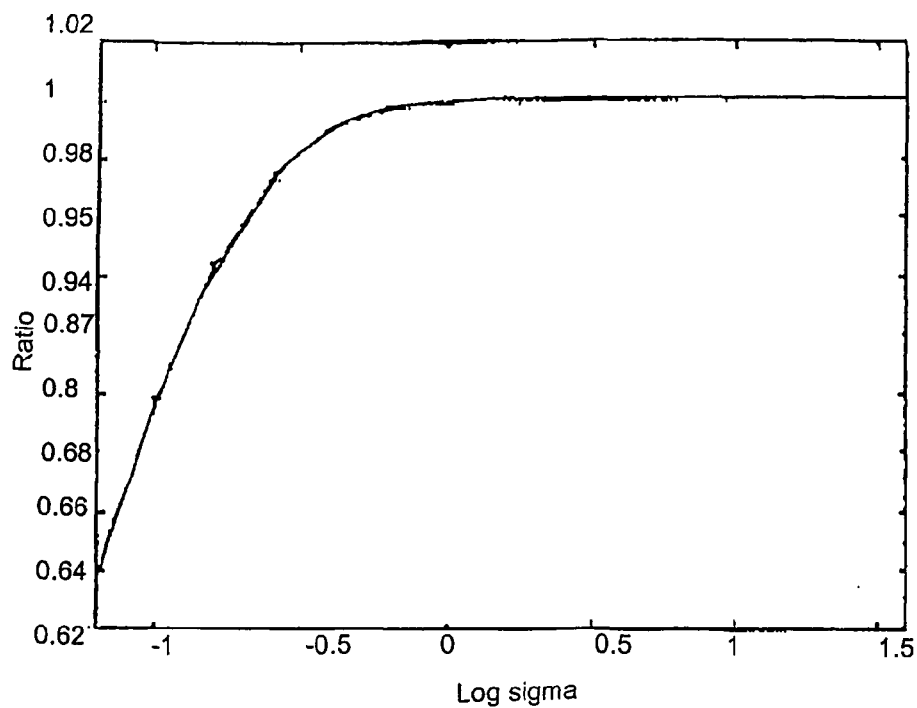
FIG. 9 is a plot of the approximation ratio of Equation 100 for different values of $\sigma$. When the ratio is near 1, there is almost no loss of information using $IH_{KPCA}$ and thus in this case ISVM and $IH_{KPCA}$ are identical.

The ISVM and $IH_{KPCA}$ methods yield almost identical performances, especially for large values of σ, which can be explained by FIG. 9. The ratio of Equation 100 has been computed for different values of a. For large values, this ratio is almost 1, which means that there is almost no loss of information by projecting $d\Phi(x_i)$ on E. Thus, ISVM and $IH_{KPCA}$ produce the same decision boundary.

The LIH method slightly impaired the performance. Nearly the same results were expected as would be obtained from a standard SVM. In this example, the covariance matrix of tangent vectors in input space should be roughly a constant times the identity matrix:

$$\sum_{i=1}^{n} dx_i dx_i^T \approx CI_2. \qquad (105)$$

Figure 10:
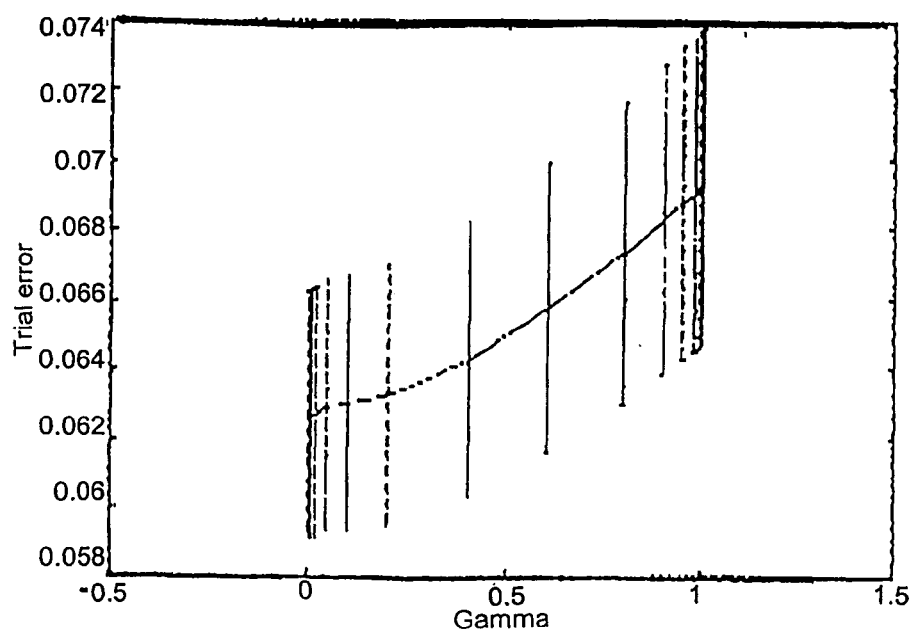
FIG. 10 is a plot of test error versus $\gamma$ for LIH. Trying to incorporate invariance using this method fails on this toy example.

Different values of γ were tried for this method, but none of them provided improvement, as shown in FIG. 10.

Figure 11:
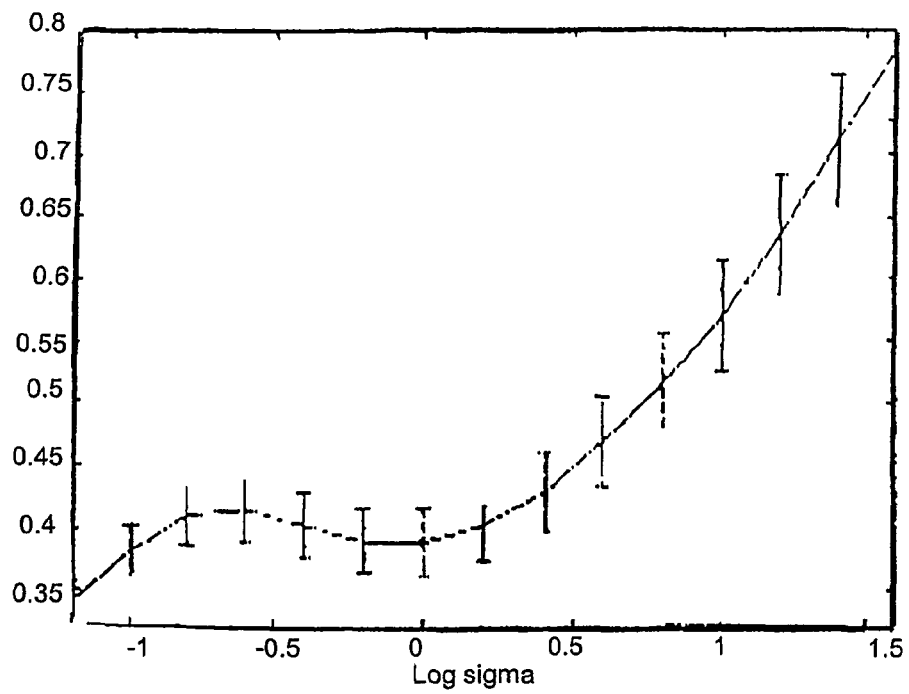
FIG. 11 is a plot of the value of the invariance enforcement part (from Equation 106 of the objective function across $\sigma$. A small value amounts to a better enforcement of the invariances.

Certain results plotted in FIG. 8a were somewhat surprising, but may be specific to this problem:
- The test error of a normal SVM does not increase when a has large values. This is not the traditional "bowl" shape.
- While the test error for SVM and VSV do not increase for large σ, the test errors of ISVM and $\text{IH}_{KPCA}$ do. Possibly a larger value of γ (more invariance) should be applied in this case. This can be seen from FIG. 11, where the following quantity has been plotted $$\sqrt{\frac{1}{n}\sum_{i=1}^{n}(w \cdot d\Phi(x_i))^2} \qquad (106)$$

However, the reason for a larger value of γ remains unclear. Note that Equation 106 gives a rule of thumb on how to select a good value for γ. Indeed, after training, a reasonable value for Equation 106 should be in the range [0.2-0.4]. This represents the average difference between the output of a training point and its transformed $\mathcal{L}_t x_i$. Referring to FIG. 8b:
- The more invariances, the better (and it converges to the same value for different σ). However, it might be due to the nature of this toy problem.
- When comparing log σ=1.4 and log σ=0, one notices that the decrease in the test error does not have the same speed. This is actually the dual of the phenomenon observed in FIG. 8a: for a same value of gamma, the test error tends to increase, when σ is larger.

Table 14 summarizes the test error of the different learning algorithms using optimal parameter settings.

TABLE 14

| SVM | VSV | LIH | ISVM | $\text{IH}_{KPCA}$ |
|---|---|---|---|---|
| 6.25 | 3.81 | 6.87 | 1.11 | 1.11 |

Example 3

Handwritten Digit Recognition

Invariances were incorporated for a hand-written digit recognition task. The USPS dataset have been used extensively in the past for this purpose by workers in the SVM field. This dataset consists of 7291 training and 2007 test examples.

According to B. Schölkopf, C. Burges, and V. Vapnik, "Extracting support data for a given task", U. M. Fayyad and R. Uthurusamy, editors, *First International Conference on Knowledge Discovery & Data* Mining. AAAI Press, 1995, the best performance has been obtained for a polynomial kernel of degree 3, $$K(x, y) = \left(\frac{x \cdot y}{256}\right)^3. \qquad (107)$$

Figure 12:
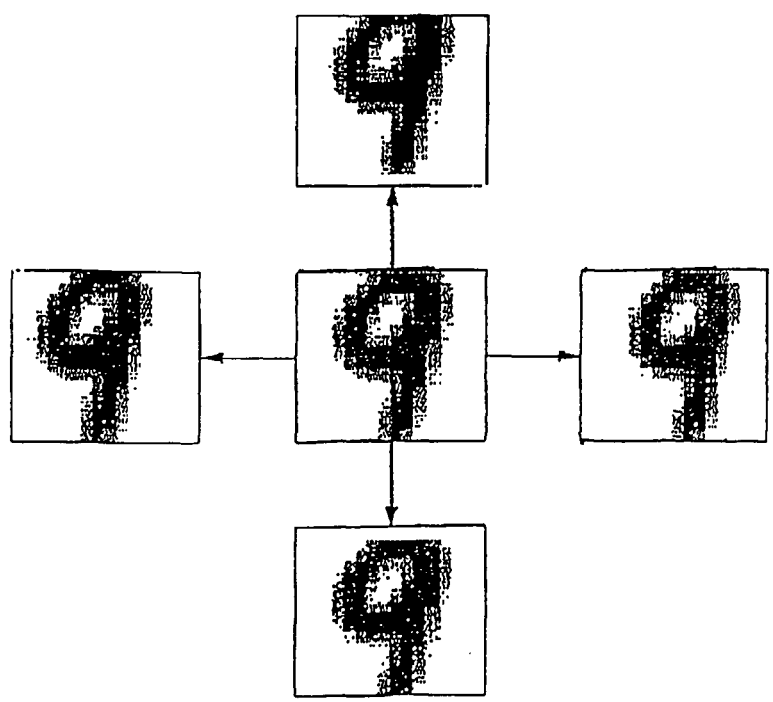
FIG. 12 illustrates the numeral 9 with the original digit in the center and as translated from 1 pixel on the left, right, up and down.

The factor 256, equaling the dimension of the data, has been included to avoid numerical instabilities. Since the choice of the base kernel is not the primary concern, the results described in this section were performed using this kernel. The local transformations are horizontal and vertical translations. All of the tangent vectors have been computed by a finite difference between the original digit and its 1-pixel translated, as shown in FIG. 12.

Following the experimental protocol described in B. Schölkopf, J. Shawe-Taylor, A. J. Smola, and R. C. Williamson, "Generalization bounds via eigenvalues of the Gram matrix", Technical Report 99-035, NeuroColt, 1999, the training set was split into 23 subsets of 317 training examples after a random permutation of the training and test set. The focus of the experiment was on a binary classification problem, namely separating digits 0 to 4 against 5 to 9. The gain in performance should also be valid for the multiclass case.

Figure 13A:
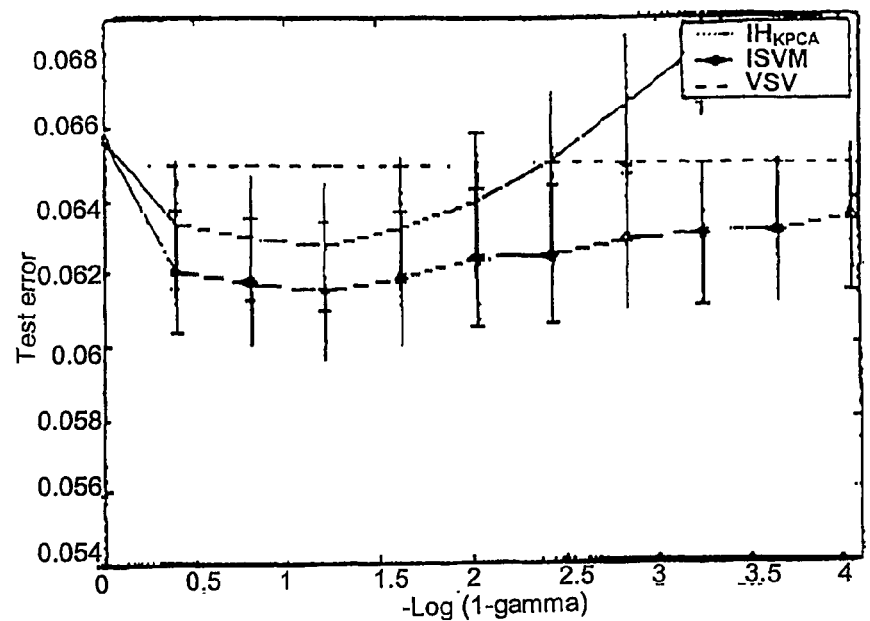
FIGS. 13a and 13b are plots comparing ISVM, $IH_{KPCA}$ and VSV on the USPS dataset, where FIG. 13a ($\gamma$=0) corresponds to standard SVM and FIG. 13b ($\gamma \to 1$) indicates significant emphasis on the enforcement of the constraints. The test errors are averaged over the 23 splits and the error bars correspond to the standard deviation of the means.
Figure 13B:
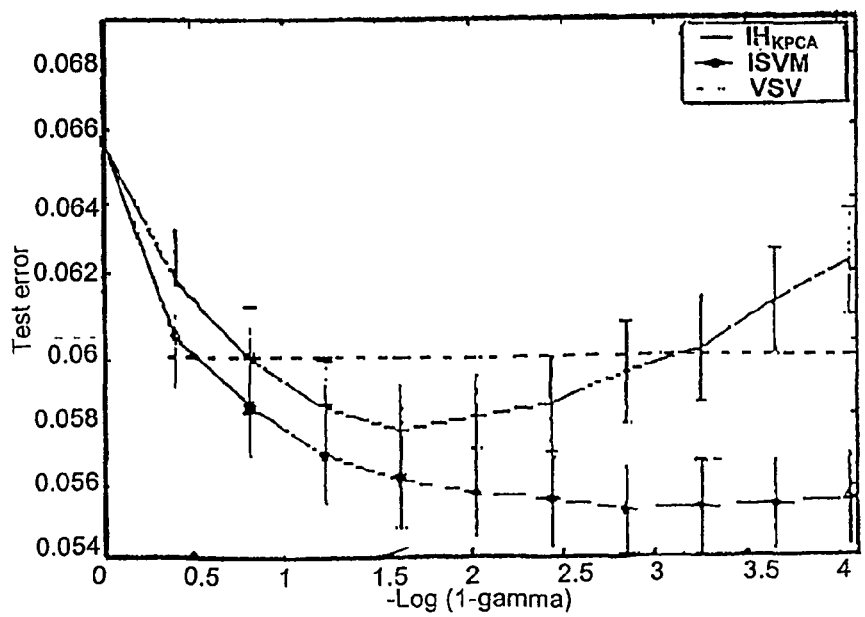

FIGS. 13a and 13b compare ISVM, $\text{IH}_{KPCA}$ and VSV for different values of γ. From these figures, it can be seen that the difference between ISVM (the original method) and $\text{IH}_{KPCA}$ (the approximation) is much larger than in the toy example. The quality of the approximation can be estimated through the approximation ratio of Equation 100. For the vertical translation, this value is 0.2. For horizontal translation, the value is 0.33. The fact that these values are much less than 1 explains the difference in performance between the 2 methods (especially when γ→1). A possible reason for the apparent performance disparity relative to the toy example (Example 2) may be due to the differences in input dimensionality. In 2 dimensions with a radial basis function (RBF) kernel, the 30 examples of the toy problem "almost span" the whole feature space, whereas with 256 dimensions, this is no longer the case.

What is noteworthy in these experiments is that the proposed method is much better than the standard VSV. The reason for this improvement may be that invariance is enforced around all training points, and not only around support vectors It should be noted that "VSV" refers to a standard SVM with a double size training set containing the original dates points and their translates.

The horizontal invariance yields larger improvements than the vertical one. This may be due to the fact that the digits in the USPS database are already centered vertically. (See FIG. 12.)

Figure 14:
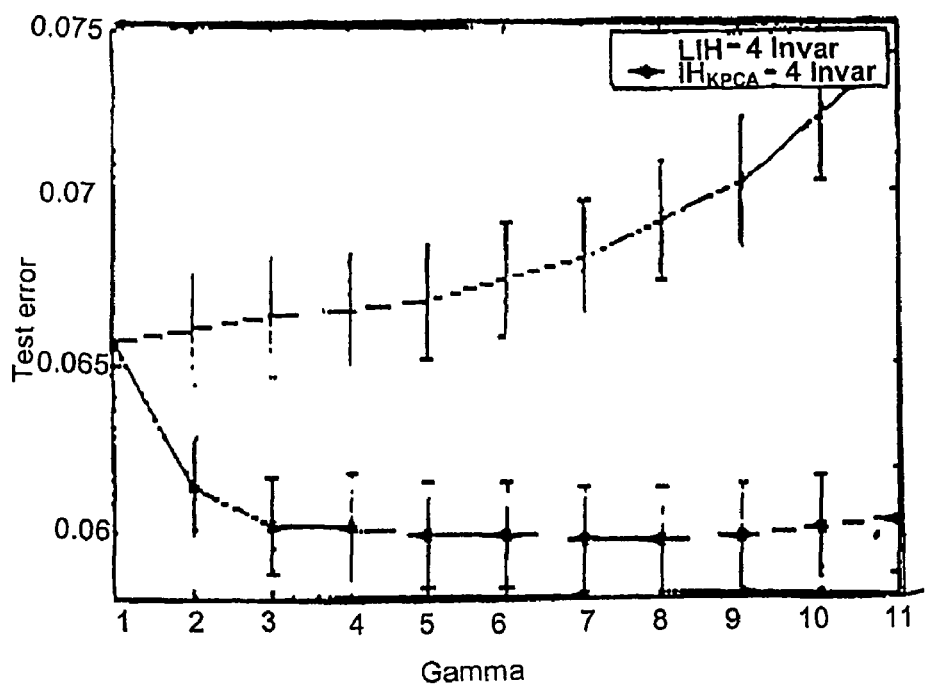
FIG. 14 shows results for 4 invariances and different values of $\gamma$.

After having studied single invariances, gain was evaluated in the presence of multiple invariances. For the digit recognition task, 4 invariances (one pixel in each direction) were considered. FIG. 14 provides a comparison of $\text{IH}_{KPCA}$ (which scales better than ISVM for multiple invariances) with LIH. As indicated, $\text{IH}_{KPCA}$ provides significant improvement in performance while LIH fails.

Example 4

Application to Noisy Measurements

The different components of a training point in input space usually correspond to some noisy measurements associated with a physical device. Ideally, the learning machine should not to be affected by this noise, i.e., the noise should not cause the output of the decision function to vary.

If the noise model were known, it would be straightforward to train such a learning machine; one could simply consider the effect of the noise as an invariant transformation and use the non-linear invariant SVM techniques described above.

In practice, one does not know the noise but can perform several measurements of the same sample. In this way, it is possible to construct "noise vectors".

Suppose that for each training sample $x_i$, p additional measurements of the one sample yielding p replicates of $x_i$, $\{x_i^{(1)}, \ldots, x_i^{(p)}\}$ are performed. One can constructs p noise vectors, $$dx_i^{(k)} = x_i^{(k)} - x_i, \ 1 \leq k \leq p. \tag{108}$$

The replicates should be seen as identical to the original training point since they are measurements of the same object.

Note that the digit recognition experiments can be considered as an instance of this problem: the camera is never positioned in such a way that the digit falls exactly in the middle of the bitmap. In other words, there is a "position noise".

The favorable results obtained in the digit recognition task prompted additional experiments on another dataset consisting of mass spectrograms. For each training sample there were two measurements, allowing construction of one noise vector. The techniques described herein yielded significant improvements over standard SVMs and the VSV method.

The method of the second embodiment of the present invention extends a method for constructing invariant hyperplanes to the nonlinear case. Results obtained with this new method are superior to the virtual SV method, the latter of which has recently broken the record on the NIST database which is the "gold standard" of handwritten digit benchmarks (see D. DeCoste and B. Schölkopf, "Training invariant support vector machines", *Machine Learning*, 2001.)

Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed:

1. A method for analyzing a dataset in data space to extract knowledge by identifying patterns in the dataset for classification of data within the dataset, wherein the dataset has an actual structure, the method comprising:

inputting structured training data into a memory of a computer comprising a processor having software stored therein for executing a kernel machine;

defining a kernel for execution by the kernel machine by:

representing the training dataset in the memory as a collection of components and an actual location of each component within the training data structure, wherein the actual location is specified as indices within an index set, each of the indices corresponding to a point of reference to the actual location;

applying a vicinity function to the collection of components to define subsets of components centered at different actual locations within the training dataset structure; and measuring a similarity of the subsets of components at the different actual locations to define a locational kernel corresponding to each actual location;

combining the locational kernels for all of the different actual locations by performing an operation to produce a kernel on a set of structures;

applying the kernel on a set of structures to the dataset in the memory to identify patterns within the datase; and storing data associated with the patterns within the dataset on a media.

2. The method of claim 1, wherein the dataset comprises data selected from the group consisting of DNA sequences, protein sequences, documents, graphs, signals, microarray expression profiles, spectra, images, spatio-temporal data and relational data.

3. The method of claim 1, wherein the step of combining the locational kernels comprises performing one or more operations selected from the group consisting of addition, scalar multiplication, multiplication, pointwise limits, argument transformations, convolution with a vicinity function and convolution with a real-valued function.

4. The method of claim 1, wherein the kernel on a set of structures is obtained by fixing the indices of the kernel given the locational kernel.

5. The method of claim 1, wherein the kernel on a set of structures is obtained by using a notion of similarity that is invariant with respect to certain transformations of the indices.

6. The method of claim 1, wherein the locational kernels comprises Gaussian radial basis function kernels having fixed indices and the kernel on a set of structures comprises a product overall all index positions of the locational kernels.

7. The method of claim 1, wherein the kernel on a set of structures further incorporates transformation invariance and the kernel is generated by estimating at least one tangent vector for associating each data point with a local invariance and selecting the kernel so that its optimization incorporates a covariance matrix of a plurality of the tangent vectors.

8. The method of claim 1, wherein the kernel further incorporates transformation invariance and the function is obtained using a kernel PCA map.

9. The method of claim 1, wherein the noise and the kernel are generated by estimating at least one noise vector associated with each data point and selecting the kernel so that its optimization incorporates a covariance matrix of a plurality of noise vectors.

10. The method of claim 1 wherein the operation includes summing the locational kernels over the indices, fixing the indices, or taking the product over all index positions of locational kernels.

11. A method for extracting knowledge from a dataset in data space, wherein the dataset has an actual structure, the method comprising:

inputting structured training data into a memory of a computer comprising a processor having software stored therein for executing a kernel machine;

representing the training data in the memory as a collection of components and a structural location of each component within the training data structure, wherein the structural location is specified as indices within an index set, wherein each of the indices corresponding to a point of reference to the structural location;

applying a vicinity function to the collection of components to define subsets of components centered at different structural locations within the training data structure;

measuring a similarity of the subsets of components at the different structural locations to define a locational kernel corresponding to each structural location;

combining the locational kernels for all of the different structural locations by performing an operation to produce a kernel on a set of structures;

applying the kernel on a set of structures in the memory to the dataset to identify patterns within the dataset; and transferring data associated with the patterns to a storage device.

12. The method of claim 11, wherein the dataset comprises data selected from the group consisting of DNA sequences, protein sequences, documents, graphs, signals, microarray expression profiles, spectra, images, spatio-temporal data and relational data.

13. The method of claim 11, wherein the step of combining the locational kernels comprises performing one or more operations selected from the group consisting of addition, scalar multiplication, multiplication, pointwise limits, argument transformations, convolution with a vicinity function and convolution with a real-valued function.

14. The method of claim 11, wherein the kernel on a set of structures is obtained by fixing the indices of the kernel given the locational kernel.

15. The method of claim 11, wherein the kernel on a set of structures is obtained by using a notion of similarity that is invariant with respect to certain transformations of the indices.

16. The method of claim 11, wherein the locational kernels comprises Gaussian radial basis function kernels having fixed indices and the product overall all index positions of the locational kernels.

17. The method of claim 11, further comprising incorporating transformation invariance by estimating at least one tangent vector for associating each data point with a local invariance and selecting the function so that its optimization incorporates a covariance matrix of a plurality of the tangent vectors.

18. The method of claim 11, further comprising incorporating transformation invariance using a kernel PCA map.

19. The method of claim 11, further comprising incorporating noise by estimating at least one noise vector associating with each data point and selecting the function so that its optimization incorporates a covariance matrix of a plurality of noise vectors.

20. The method of claim 11 wherein the operation includes summing the locational kernels over the indices, fixing the indices, or taking the product over all index positions of locational kernels.

21. A method for analyzing a pair of structured objects to identify patterns within the pair of structure objects for classification of the structured objects, wherein each structured object comprises a dataset, the method comprising:

inputting a training dataset into a memory of a computer having a processor for executing a kernel machine, wherein the training dataset comprises structured objects;

representing each structured object in the training dataset in the memory as a collection of component objects and a structural location of a set of indices within the structured object each of the indices corresponding to a point of reference to the structural location;

applying a vicinity function to the collection of component objects to define subsets of component objects centered at different indices within each structured object in the training dataset; and measuring a similarity between the subsets of component objects of one structured object of the training dataset and the subsets of components objects of the another structured object of the training dataset to define a locational kernel corresponding to each of the different indices;

combining the locational kernels for all of the different indices by performing an operation to produce a kernel on a set of structured objects;

applying the kernel on a set of structures in the memory to the pair of structured objects to identify patterns within the pair of structure objects; and displaying data associated with the patterns on a display device.

22. The method of claim 21, wherein the structured object is of a type selected from the group consisting of strings, DNA sequences, protein sequences, documents, trees, graphs, signals, microarray expression profiles, spectra, images, spatio-temporal data and relational data.

23. The method of claim 21 wherein the operation includes summing the locational kernels over the indices, fixing the indices, or taking the product over all index positions of locational kernels.

* * * * *